United States Patent
Koeberl et al.

(10) Patent No.: US 11,690,812 B2
(45) Date of Patent: Jul. 4, 2023

(54) METHODS AND COMPOSITIONS FOR THE TREATMENT OF STEATOSIS-ASSOCIATED DISORDERS

(71) Applicants: Duke University, Durham, NC (US); National University of Singapore, Singapore (SG)

(72) Inventors: Dwight D. Koeberl, Durham, NC (US); Paul M. Yen, Singapore (SG); Benjamin L. Farah, Rocky River, OH (US)

(73) Assignees: Duke University, Durham, NC (US); National University of Singapore, Singapore (SG)

( * ) Notice: Subject to any disclaimer, the term of this patent is extended or adjusted under 35 U.S.C. 154(b) by 86 days.

(21) Appl. No.: 17/190,018

(22) Filed: Mar. 2, 2021

(65) Prior Publication Data

US 2021/0251922 A1  Aug. 19, 2021

Related U.S. Application Data

(62) Division of application No. 15/760,156, filed as application No. PCT/US2016/052249 on Sep. 16, 2016, now Pat. No. 10,940,125.

(60) Provisional application No. 62/220,701, filed on Sep. 18, 2015.

(51) Int. Cl.
| | |
|---|---|
| *A61K 31/137* | (2006.01) |
| *A61K 31/436* | (2006.01) |
| *A61K 31/05* | (2006.01) |
| *A61K 31/155* | (2006.01) |
| *A61K 31/192* | (2006.01) |
| *A61K 38/47* | (2006.01) |
| *A61K 31/522* | (2006.01) |
| *A61K 38/46* | (2006.01) |
| *A61K 31/198* | (2006.01) |
| *A61K 31/12* | (2006.01) |
| *A61K 31/216* | (2006.01) |
| *A61K 31/352* | (2006.01) |
| *A61K 31/167* | (2006.01) |
| *A61P 3/00* | (2006.01) |
| *A61K 31/277* | (2006.01) |
| *A61K 31/355* | (2006.01) |
| *A61K 31/385* | (2006.01) |
| *A61K 31/5415* | (2006.01) |
| *A61K 31/55* | (2006.01) |
| *A61K 31/575* | (2006.01) |

(Continued)

(52) U.S. Cl.
CPC ............ *A61K 31/137* (2013.01); *A61K 31/05* (2013.01); *A61K 31/12* (2013.01); *A61K 31/155* (2013.01); *A61K 31/167* (2013.01); *A61K 31/192* (2013.01); *A61K 31/198* (2013.01); *A61K 31/216* (2013.01); *A61K 31/277* (2013.01); *A61K 31/352* (2013.01); *A61K 31/355* (2013.01); *A61K 31/385* (2013.01); *A61K 31/436* (2013.01); *A61K 31/522* (2013.01); *A61K 31/5415* (2013.01); *A61K 31/55* (2013.01); *A61K 31/575* (2013.01); *A61K 31/7016* (2013.01); *A61K 33/00* (2013.01); *A61K 38/465* (2013.01); *A61K 38/47* (2013.01); *A61P 3/00* (2018.01); *C12Y 301/04012* (2013.01); *C12Y 302/0102* (2013.01); *C12Y 302/01022* (2013.01); *C12Y 302/01045* (2013.01); *C12Y 302/01049* (2013.01); *C12Y 302/01076* (2013.01)

(58) Field of Classification Search
CPC .... A61K 31/137; A61K 31/05; A61K 31/155; A61K 31/192; A61K 31/277; A61K 31/355; A61K 31/385; A61K 31/436; A61K 31/5415; A61K 31/55; A61K 31/575; A61K 31/7016; A61K 33/00; A61K 38/47; A61P 3/00; C12Y 302/0102
See application file for complete search history.

(56) References Cited

U.S. PATENT DOCUMENTS

| | | | |
|---|---|---|---|
| 5,236,838 A | 8/1993 | Rasmussen et al. | |
| 5,382,524 A | 1/1995 | Desnick et al. | |
| 5,401,650 A | 3/1995 | Desnick et al. | |

(Continued)

FOREIGN PATENT DOCUMENTS

| | | |
|---|---|---|
| WO | 9310244 A1 | 5/1993 |
| WO | 0012740 A2 | 3/2000 |

(Continued)

OTHER PUBLICATIONS

Farah BL, Landau DJ, Sinha RA, Brooks ED, Wu Y, Fung SYS, Tanaka T, Hirayama M, Bay BH, Koeberl DD, Yen PM. Induction of autophagy improves hepatic lipid metabolism in glucose-6-phosphatase deficiency. J Hepatol. Feb. 2016;64(2):370-379. doi: 10.1016/j.jhep.2015.10.008. Epub Oct. 20, 2015. PMID: 26462884.*

(Continued)

*Primary Examiner* — Kade Ariani
(74) *Attorney, Agent, or Firm* — Polsinelli PC

(57) ABSTRACT

The present disclosure is directed to methods of treating a steatosis-associated disorder by administering a therapeutic agent selected from a lysosomal enzyme, an autophagy-inducing agent, or a combination thereof. Steatosis-associated disorders discussed herein include GSD Ia, GSD Ib, GSD Ic, NAFLD, and NASH. Other embodiments are directed to methods of reversing steatosis, modulating autophagy, inducing autophagy, and reversing glycogen storage.

19 Claims, 23 Drawing Sheets

(51) Int. Cl.
A61K 31/7016 (2006.01)
A61K 33/00 (2006.01)

(56) References Cited

U.S. PATENT DOCUMENTS

| | | | |
|---|---|---|---|
| 5,686,240 | A | 11/1997 | Schuchman et al. |
| 5,879,680 | A | 3/1999 | Ginns et al. |
| 7,056,712 | B2 | 6/2006 | Chen |
| 2002/0110551 | A1 | 8/2002 | Chen |
| 2004/0081645 | A1 | 4/2004 | Van Bree et al. |
| 2006/0069070 | A1 | 3/2006 | Fiorucci et al. |
| 2009/0182022 | A1 | 7/2009 | Rongen et al. |
| 2009/0232879 | A1 | 9/2009 | Cable et al. |
| 2011/0104187 | A1 | 5/2011 | Chen et al. |
| 2012/0082653 | A1 | 4/2012 | Koeberl |
| 2014/0315781 | A1 | 10/2014 | Lee et al. |

FOREIGN PATENT DOCUMENTS

| | | |
|---|---|---|
| WO | 2013134530 A1 | 9/2013 |
| WO | 2014130722 A1 | 8/2014 |
| WO | 2014130723 A1 | 8/2014 |
| WO | 2014151950 A1 | 9/2014 |
| WO | 2015062738 A1 | 5/2015 |
| WO | 2015157697 A1 | 10/2015 |

OTHER PUBLICATIONS

Grygiel-Górniak, B. Peroxisome proliferator-activated receptors and their ligands: nutritional and clinical implications—a review. Nutr J 13, 17 (2014). https://doi.org/10.1186/1475-2891-13-17.*
Bandsma R.H.J., et al., "Disturbed Lipid Metabolism in Glycogen Storage Disease Type 1," European Journal of Pediatrics, vol. 161, 2002, pp. S65-S69.
Coppola M., et al., "Thyroid Hormone Analogues and Derivatives: Actions in Fatty Liver," World Journal of Hepatology, 2014, vol. 6(3), pp. 114-129.
International Preliminary Report on Patentability for the Application No. PCT/US2016/052249 dated Mar. 20, 2018 (Applicant—Duke University // Inventors—Dwight Koeberl, et al.) (8 pages).
International Search Report and Written Opinion for PCT/US2016/052249 dated Dec. 7, 2016 (Applicant—Duke University // Inventors—Dwight Koeberl, et al.) (9 Pages).
Lin C., et al., "Pharmacological Promotion of Autophagy Alleviates Steatosis and Injury in Alcoholic and Non-alcoholic Fatty Liver Conditions in Mice," Journal of Hepatology, vol. 58(5), May 2013, pp. 993-999.
Gonzalez-Rodriguez A., et al., "Impaired Autophagic Flux is Associated with Increased Endoplasmic Reticulum Stress during the Development of NAFLD," Cell Death and Disease, vol. 5, 2014, pp. 1-13, e1179.
Silva B.D., et al., "Singular Effects of PPAR Agonists on Nonalcoholic Fatty Liver Disease of Diet-Induced Obese Mice," Life Sciences, 2015, vol. 127, pp. 73-81.
Wermuth C.G., "Similarity in Drugs: Reflections on Analogue Design," Drug discovery Today, 2006, vol. 11, No. 7/8, pp. 348-354.
Amalfitano A., et al., "Recombinant Human Acid Alpha-glucosidase Enzyme Therapy for Infantile Glycogen Storage Disease Type Ii: Results of a Phase I/II Clinical Trial," Genet. Med. 2001 3(2):132-138.
Arad et al., "Constitutively active AMP kinase mutations cause glycogen storage disease mimicking hypertrophic cardiomyopathy," J Clin Invest, 109(3):357-62, Feb. 2002.
Buhrer et al., "Fetal bradycardia at 28 weeks of gestation associated with cardiac glycogen phosphorylase b kinase deficiency," Acta Paediatr, 92(11): 1352-3, Nov. 2003.
Burwinkel et al. "Fatal congenital heart glycogenosis caused by a recurrent activating R531Q mutation in the gamma 2-subunit of AMP-activated protein kinase (PRKAG2), not by phosphorylase kinase deficiency," Am J Hum Genet, 76 (6): 1034-49, May 2005.

Chou et al., "Glycogen storage disease type I and G6Pase-β deficiency: etiology and therapy", Nat Rev Endocrinol., Dec. 2010, vol. 6, No. 12, pp. 676-688.
Extended European Search Report for Application No. EP16842895.1 dated Jan. 31, 2019 (Applicant—Duke University // Inventors—Kishnani et al.) (9 pages).
Fuller, M. et al., "Isolation and characterisation of a recombinant, precursor form of lysosomal acid alpha-glucosidase," Eur. J. Biochem. 234:903 909 (1995).
Gollob et al., "Novel PRKAG2 mutation responsible for the genetic syndrome of ventricular preexcitation and conduction system disease with childhood onset and absence of cardiac hypertrophy," Circulation, 104(25): 3030-3, Dec. 2001.
Written Opinion for PCT/US2016/049680 dated Nov. 16, 2016 (Inventors—Kishnani et al. // Applicant—Duke University) (5 pages).
International Search Report for PCT/US2016/049680 dated Nov. 16, 2016 (Inventors—Kishnani et al. // Applicant—Duke University) (2 pages).
Laforet et al. "A new mutation in PRKAG2 gene causing hypertrophic cardiomyopathy with conduction system disease and muscular glycogenosis," Neuromuscul Disord, 16(3):178-82, Mar. 2006.
Lin C., et al., "Pharmacological Promotion of Autophagy Alleviates Steatosis and Injury in Alcoholic and Non-alcoholic Fatty Liver Conditions in Mice," Journal of Hepatology, vol. 58(5), May 2013, pp. 993-999, doi: 10.1016/j.jhep.2013.01.011.
Mendelsohn N.J., et al., "Elimination of Antibodies to Recombinant Enzyme in Pompe's Disease," The New England Journal Medicine, Jan. 8, 2009, vol. 360(2), pp. 194-195.
Ozen et al., "Glycogen storage diseases: New perspectives", World J Gastroenterol., May 14, 2007, vol. 13, No. 18, pp. 2541-2553.
Raben et al: "Enzyme replacement therapy in the mouse model of Pompe disease," Molecular Genetics and Metabolism, vol. 80, No. 1-2, Sep. 1, 2003 (Sep. 1, 2003), pp. 159-169.
Regalado et al., "Infantile hypertrophic cardiomyopathy of glycogenosis type IX: isolated cardiac phosphorylase kinase deficiency," Pediatr Cardiol. Jul.-Aug. 1999; 20(4):304-7.
Gonzalez-Rodriguez, et al., "Impaired Autophagic Flux is Associated with Increased Endoplasmic Reticulum Stress during the Development of NAFLD," Cell Death and Disease, vol. 5, 2014, pp. 1-13, e1179.
Strothotte et al: "Enzyme replacement 1-15 therapy with alglucosidase alfa in 44 patients with late-onset glycogen storage disease type 2:12-month results of an observational clinical trial",Journal of Neurology—Zeitschrift Fuer Neurologie, vol. 257, No. 1, Aug. 1, 2009 (Aug. 1, 2009), pp. 91-97.
Sun et al., "Alglucosidase alfa enzyme replacement therapy as a therapeutic approach for glycogen storage disease type III", Molecular Genetics and Metabolism, Feb. 2013, vol. 108, No. 2, pp. 145-147.
Van Hove, J. L. K. et al., "High-level production of recombinant human lysosomal acid alpha-glucosidase in Chinese hamster ovary cells which targets to heart muscle and corrects glycogen accumulation in fibroblasts from patients with Pompe disease," Proc. Natl. Acad. Sci. USA 93:65 70 (1996).
Weledji: "Paediatric Metabolic Conditions of the Liver", EMJ Hepatology, Jan. 2015, vol. 3, No. 1, pp. 55-62.
Xu et al.: "Improved efficacy of gene therapy approaches for Pompe disease using a new, immune-deficient GSD-II mouse model", Gene Therapy, vol. 11, No. 21, Nov. 1, 2004 (Nov. 1, 2004), pp. 1590-1598.
Zhang et al., "Single-nucleotide polymorphisms of the PRKCG gene and osteosarcoma susceptibility," Tumour Bio, 35(12): 12671-7, Sep. 2014.
Zhang et al. "Overexpression of G100S mutation in PRKAG2 causes Wolff-Parkinson-White syndrome in zebrafish," ClinGenet, 86(3):287-91, Oct. 2013.
International Preliminary Report of Patentability for PCT/US2016/049680 dated Mar. 6, 2018 (Inventors—Kishnani et al. // Applicant—Duke University) (6 pages).

* cited by examiner

METHODS AND COMPOSITIONS FOR THE TREATMENT OF STEATOSIS-ASSOCIATED DISORDERS

CROSS-REFERENCE TO RELATED APPLICATIONS

This application is a divisional application of U.S. application Ser. No. 15/760,156 filed Mar. 14, 2018, which is a U.S. national phase application under 35 U.S.C. § 371 of International Application No. PCT/US2016/052249 filed Sep. 16, 2016, which claims the benefit of priority to both U.S. Provisional Application No. 62/220,701 filed Sep. 18, 2015 and International Application No. PCT/US2016/049680 filed on Aug. 31, 2016, the disclosure of each of which is incorporated by reference herein in its entirety.

STATEMENT REGARDING FEDERALLY SPONSORED RESEARCH OR DEVELOPMENT

This invention was made in part with government support under Grant No. 5R01DK105434 awarded by the National Institutes of Health. The Government has certain rights in this invention.

SUMMARY

Embodiments herein are directed to treating a steatosis-associated disorder in a subject in need thereof, the method comprising administering to the subject a therapeutic agent of embodiments herein. In some embodiments, the therapeutic agent is an autophagy-inducing agent, a lysosomal enzyme, or a combination thereof. Some embodiments herein are directed to a method of reversing steatosis in a subject in need thereof, the method comprising administering to the subject a therapeutic agent of embodiments herein. Some embodiments herein are directed to a method of reversing glycogen storage in a subject in need thereof, the method comprising administering to the subject a therapeutic agent of embodiments herein. Some embodiments herein are directed to a method of modulating autophagy in a subject in need thereof, the method comprising administering to the subject a therapeutic agent of embodiments herein. Some embodiments herein are directed to a method of inducing autophagy in a subject in need thereof, the method comprising administering to the subject a therapeutic agent of embodiments herein. In some embodiments, the subject has a steatosis-associated disorder.

Some embodiments herein are directed to a method of treating Glycogen Storage Disease Type I (GSD I) to a subject in need thereof, the method comprising administering to the subject a therapeutic agent of embodiments described herein. In some embodiments, the GSD I is selected from GSD Ia, GSD Ib, or GSD Ic. In some embodiments, the GSD I is GSD Ia. Some embodiments herein are directed to a method of treating non-alcoholic fatty liver disease (NAFLD) to a subject in need thereof, the method comprising administering to the subject a therapeutic agent of embodiments described herein. Some embodiments herein are directed to a method of treating non-alcoholic steatohepatitis (NASH) to a subject in need thereof, the method comprising administering to the subject a therapeutic agent of embodiments described herein.

In some embodiments, the therapeutic agent may be a lysosomal enzyme, an autophagy-inducing agent, or a combination thereof. In some embodiments, the above methods may comprise administering a lysosomal enzyme and an autophagy-inducing agent.

In some embodiments, the autophagy-inducing agent may be selected from a thyroid hormone, mTOR inhibitor, caffeine (trimethylxanthine), PPAR-α agonist, AMPK activator, a beta 2 adrenergic agonist (β2 agonist), calcium channel blocker, chemical chaperone, intracellular isositol reducer, Sirtuin-1 activator, sarnesoid X receptor suppressor, or a combination thereof. In some embodiments, the mTOR inhibitor may be selected from rapamycin, Torin1, temsirolimus (CCI-779), everolimus (RAD001), and ridaforolimus (AP-23573), Deforolimus (AP23573, MK-8669), mTORC1/mTORC2 dual inhibitor (e.g. PP242 WYE354), mTOR/P13K dual inhibitor (e.g. PI103 NVP-BEZ235), an analog thereof, or a combination thereof. In some embodiments, the AMPK activator may be selected from 5-Aminoimidazole-4-carboxamide ribonucleotide (AICAR), quercetin, α-lipoic acid, R-lipoic acid, metformin, resveratrol, guanidine, biguanidine, galegine, ginsenoside, curcumin, berberine, epigallocatechin gallate, theaflavin, hispidulin, a salicylate, a prodrug thereof, or a combination thereof. In some embodiments, the PPAR-α agonist may be selected from bezafibrate, genofibrate, ciprofibrate, gemfibrozil, clofibrate, an analog thereof, or a combination thereof. In some embodiments, the thyroid hormone may be selected from thyroxine (T4), triiodothyronine (T3), an analog thereof, or a combination thereof. In some embodiments, the ($\beta$2 agonist is albuterol, arbutamine, bambuterol, befunolol, bitolterol, bromoacetylalprenololmenthane, broxaterol, carbuterol, cimaterol, cirazoline, clenbuterol, clorprenaline, denopamine, dioxethedrine, dopexamine, ephedrine, epinephrine, etafedrine, ethylnorepinephrine, etilefrine, fenoterol, formoterol, hexoprenaline, higenamine, ibopamine, isoetharine, isoproterenol, isoxsuprine, mabuterol, metaproterenol, methoxyphenamine, norepinephrine, nylidrin, oxyfedrine, pirbuterol, prenalterol, procaterol, propranolol, protokylol, quinterenol, ractopamine, reproterol, rimiterol, ritodrine, salmefamol, soterenol, salmeterol, terbutaline, tretoquinol, tulobuterol, xamoterol, zilpaterol, zinterol, or a combination thereof. In some embodiments, the ($\beta$2 agonist may be clenbuterol. In some embodiments, the calcium channel blocker may be verapamil. In some embodiments, the chemical chaperone may be trehalose. In some embodiments, the intracellular inositol reducer may be carbamazepine, lithium chloride, or a combination thereof. In some embodiments, the Sirtuin-1 activator may be methylene blue, resveratrol, or a combination thereof. In some embodiments, samesoid X receptor suppressor may be mifepristone. In some embodiments, the autophagy inducing agent is not a B2 agonist. In some embodiments, the autophagy inducing agent induces autophagy. In some embodiments, the β2 agonist induces autophagy.

Some embodiments herein are directed to treating a steatosis-associated disorder, the method comprising administering a β2 agonist to a subject in need thereof. Some embodiments herein are directed to a method of treating GSD I, the method comprising administering a β2 agonist to a subject in need thereof. Some embodiments herein are directed to a method of treating GSD Ia, the method comprising administering a β2 agonist to a subject in need thereof. Some embodiments herein are directed to a method of treating GSD Ib, the method comprising administering a β2 agonist to a subject in need thereof. Some embodiments herein are directed to a method of treating GSD Ic, the method comprising administering a β2 agonist to a subject in need thereof. Some embodiments herein are directed to a method of treating NAFLD, the method comprising administering a β2 agonist to a subject in need thereof. Some embodiments herein are directed to a method of treating NASH, the method comprising administering a β2 agonist to a subject in need thereof.

In some embodiments, the lysosomal enzyme may be selected from glucocerebrosidase, alpha-glucosidase (acid alpha-glucosidase or GAA), alpha-galactosidase, alpha-n-acetylgalactosaminidase, acid sphingomyelinase, alpha-iduronidase, or a combination thereof. In some embodiments, the lysosomal enzyme may be acid α-glucosidase. In some embodiments, the acid alpha-glucosidase may be selected from a GAA, recombinant human acid alpha-glucosidase (rhGAA), alglucosidase alfa, neo-rhGAA, reveglucosidase alpha, an rhGAA administered with a chaperone (e.g. 1-deoxynojirimycin (DNJ), α-homonojirimycin, or castanospermine), or a combination thereof.

Some embodiments are directed to a composition comprising a therapeutic agent of embodiments herein, and a pharmaceutically acceptable excipient. In some embodiments, the therapeutic agent may be an autophagy-inducing agent, a lysosomal enzyme or a combination thereof. In some embodiments, the composition may include a lysosomal enzyme of embodiments herein and an autophagy-inducing agent of embodiments herein. Some embodiments are directed to a composition comprising an autophagy-inducing agent of embodiments herein, and a pharmaceutically acceptable excipient. Some embodiments are directed to a composition comprising a lysosomal enzyme of embodiments herein, and a pharmaceutically acceptable excipient. Some embodiments are directed to a composition comprising a β2 agonist and an acid alpha-glucosidase. Some embodiments are directed to a method of treating a steatosis-associated disorder comprising administering a composition comprising a therapeutic agent of embodiments herein, and a pharmaceutically acceptable excipient. In some embodiments, the steatosis-associated disorder may be GSD I, NAFLD, NASH, or a combination thereof. In some embodiments, GSD I may be selected from GSD Ia, GSD Ib, or GSD Ic. In some embodiments, GSD I is GSD Ia.

DESCRIPTION OF THE FIGURES

FIG. 1(A) illustrates decreased LC3-II/Actin ratio, which indicates downregulation of autophagy. FIG. 1(B) illustrates that key autophagy related proteins, ATG5 and Beclin-1, are downregulated in G6Pase (−/−) mice (n=3 per group). Mean+/−SEM. Asterisk represents p<0.05.

FIG. 2(A) illustrates LC3-II levels 96 hours after knockdown. FIG. 2(B) illustrates changes in mTOR and AMPK pathways at this timepoint (n=3, asterisk represents p<0.05).

FIGS. 3(A) and 3(B) illustrate that the upstream pro-autophagic AMPK signaling pathway is downregulated (pAMPK, pRaptor and pACC levels), and the anti-autophagic mTOR pathway (p-p70s6k levels) is upregulated in AML-12 cells treated with siG6PC (FIG. 3(A)) and G6Pase-KO mice (FIG. 3(B)). FIG. 3(C) illustrates that overexpression of constitutively active AMPK (CA-AMPK) in G6PC KD cells restores LC3-II levels. For all experiments shown n=3, *=p<0.05 between control and KD or KO groups, error bars represent SEM.

FIG. 4(A) illustrates that bodipy staining detected lipids in siG6PC treated cells. FIG. 4(B) illustrates that electron microscopy detected lipid deposits (LD) in siG6PC treated cells.

FIG. 5(A) illustrates p70s6k phosphorylation. FIG. 5(B) illustrates LC3-II protein levels. FIG. 5(C) illustrates hepatic TG levels. FIG. 5(D) illustrates representative hepatic electron micrographs at 3000×. Green arrowhead represents lipid droplets. FIG. 5(E) illustrates glycogen content. For all parts: n=4 or 5 mice per group, asterisk represents p<0.05, two asterisks represent p<0.01.

FIG. 7(A) illustrates that LC3-II was reduced in the liver of dogs with GSDIa, in comparison with unaffected carrier dogs. FIG. 7(B) and FIG. 7(C) illustrate that liver length (FIG. 7(B)) and serum GGT (FIG. 7(C)) were reduced following rapamycin treatment. *=p<0.05.

FIG. 8(A) and FIG. 8(B) illustrates that clenbuterol increases LC3-II 24 hours after addition in HepG2 cells, at concentrations as low as 300 nM. FIG. 8(C) illustrates that clenbuterol increases LC3-II 24 hours after ion in mouse primary hepatocytes. Asterisk indicates p<0.05.

FIG. 9(A) illustrates that in lysosomal storage disorders the CI-MPR is expressed at low levels on the cell membrane, and therefore a drug that increased CI-MPR would enhance biochemical correction from ERT. FIG. 9(B) illustrates that a selective β2-agonist, clenbuterol, increased CI-MPR expression and significantly enhanced biochemical correction in combination with ERT, in comparison with ERT alone, as demonstrated by decreased glycogen storage in mice with a classical lysosomal storage disorder, Pompe disease.

FIG. 10(A) Western blotting G6pc−/− mouse livers showed decreased LC3-II levels versus WT mice. FIG. 10(B) ATG5 protein level is reduced in the livers G6pc KO mice. FIG. 10(C) Beclin 1 protein level is reduced in the livers of the same mice. For all experiments shown, n=3, except (A), where n=7, and * represents p<0.05 between experimental groups being compared. Error bars: SEM.

FIG. 24(A) Representative abdominal radiograph of GSD Ia canine after 10 days of rapamycin treatment. FIG. 24(B) Ventral and dorsal lengths of livers from GSD Ia canines as measured from radiographs pre- and post-rapamycin treatment. N=4, and * indicates p<0.05.

DETAILED DESCRIPTION

Figure 1:
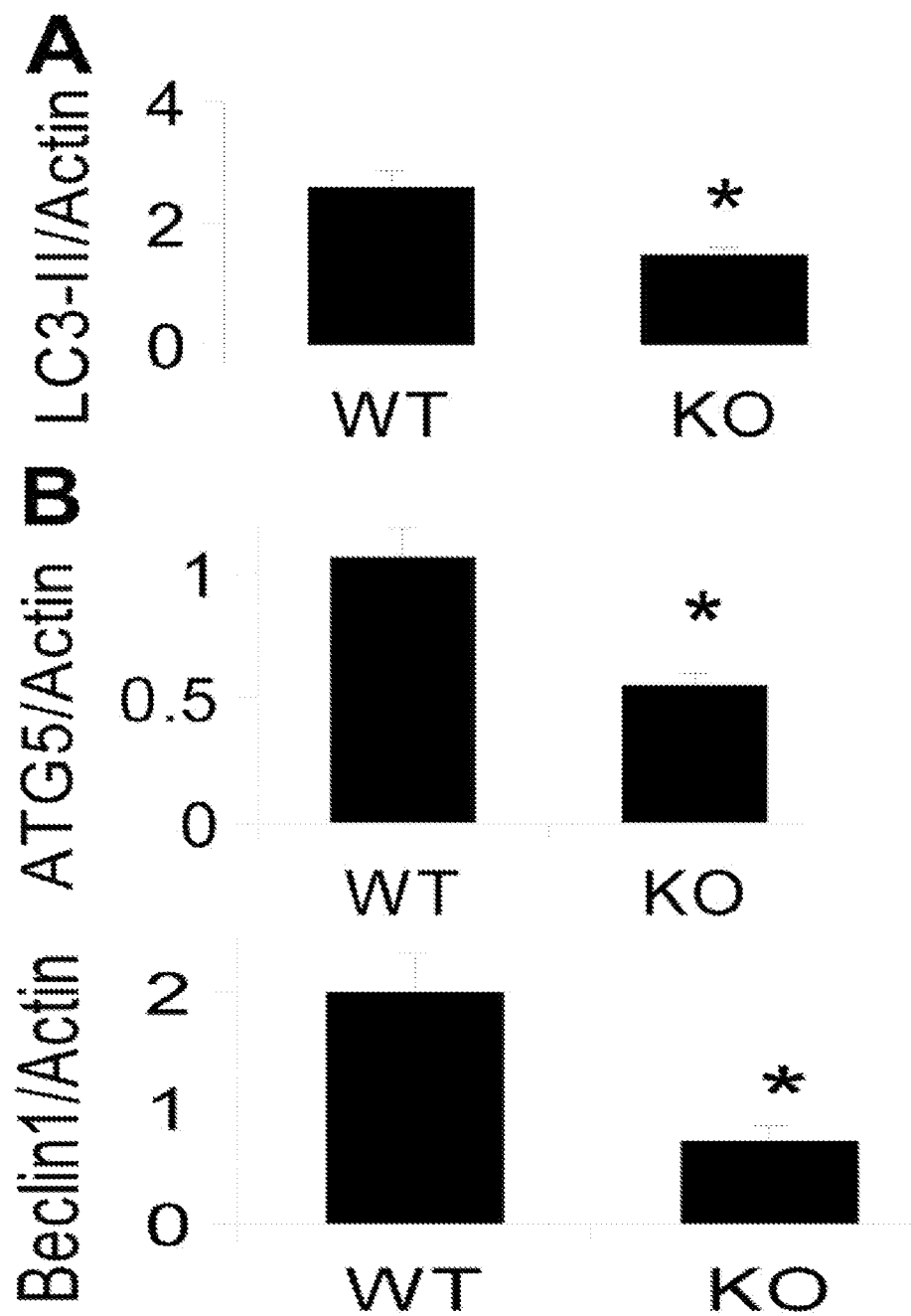
FIG. 1 illustrates the downregulation of autophagy in the GSD Ia liver.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

The present disclosure is directed to inducing autophagy in a subject having a steatosis-associated disorder, such as GSD I, NASH, or NAFLD, and reversing glycogen storage and steatosis in the subject. In some embodiments, GSD I may be selected from GSD Ia, GSD Ib, or GSD Ic. In some embodiments, the GSD I is GSD Ia. Accordingly, embodiments of the present disclosure are directed to methods of treating a steatosis-associated disorder comprising administering a therapeutic agent to a subject in need thereof. In some embodiments, the therapeutic agent is an autophagy-inducing agent.

It must also be noted that as used herein and in the appended claims, the singular forms "a", "an", and "the" include plural reference unless the context clearly dictates otherwise. Thus, for example, reference to a "β2 agonist" is a reference to one or more β2 agonists and equivalents thereof known to those skilled in the art, and so forth.

As used herein, the term "about" means plus or minus 5% of the numerical value of the number with which it is being used. Therefore, about 50% means in the range of 45%-55%.

"Administering", when used in conjunction with a therapeutic, means to administer a therapeutic directly into or onto a target tissue or to administer a therapeutic to a subject, whereby the therapeutic positively impacts the tissue to which it is targeted. Thus, as used herein, the term "administering", when used in conjunction with a therapeutic, can include, but is not limited to, providing a therapeutic to a subject systemically by, for example, intravenous injection, whereby the therapeutic reaches the target tissue. Administering a composition or therapeutic may be accomplished by, for example, injection, oral administration, topical administration, or by these methods in combination with other known techniques. Such combination techniques may include heating, radiation, ultrasound and the use of delivery agents. Preferably, administering is a self-administration, wherein the therapeutic or composition is administered by the subject themselves. Alternatively, administering may be administration to the subject by a health care provider.

The terms, "treat" and "treatment," as used herein, refer to amelioration of one or more symptoms associated with the disease, prevention or delay of the onset of one or more symptoms of the disease, and/or lessening of the severity or frequency of one or more symptoms of the disease. For example, treatment can refer to of the individual affected by the disease, or any combination of these effects. Further, the treatment may prevent long term complications such as chronic liver disease, metabolic syndrome, cirrhosis, and fibrosis. In some embodiments, treatment includes improvement of liver symptoms, particularly, in reduction or prevention of GSD (e.g., GSD-Ia)-associated hepatosteatosis, abdominal discomfort, elevated liver enzyme levels, fatigue, malaise, hepatomegaly, hyperlipidemia, hypoglycemia, hypertension, iron-resistant anemia, kidney stones, growth delay, lactic academia, nephropathy, hepatic/renal glycogenosis, pancreatitis, hepatic adenomata, hepatocellular carcinoma, osteopenia/osteoporosis, platelet dysfunction, spider angiomata, ascites, splenomegaly, hard liver border, palmar erythema, or asterixis.

The terms, "improve," "prevent" or "reduce," as used herein, indicate values that are relative to a baseline measurement, such as a measurement in the same individual prior to initiation of the treatment described herein, or a measurement in a control individual (or multiple control individuals) in the absence of the treatment described herein. A control individual is an individual afflicted with the same form of the disease (e.g., GSD-Ia) as the individual being treated, who is about the same age as the individual being treated (to ensure that the stages of the disease in the treated individual and the control individual(s) are comparable).

As used herein, the term "therapeutic agent" means an agent utilized to treat, combat, ameliorate, prevent or improve an unwanted condition or disease of a subject. In part, embodiments described herein may be directed to the treatment of various steatosis-associated disorders, including, but not limited to GSD I, NAFLD, NASH, or a combination thereof. In some embodiments, GSD I may be selected from GSD Ia, GSD Ib, or GSD Ic. In some embodiments, GSD I is GSD Ia.

The terms "therapeutically effective" or "effective", as used herein, may be used interchangeably and refer to an amount of a therapeutic composition of embodiments described herein. For example, a therapeutically effective amount of a composition is an amount of the composition, and particularly the active ingredient, such as GAA, that generally achieves the desired effect. For example, the desired effect can be an improvement, prevention, or reduction of a particular disease state.

A "therapeutically effective amount" or "effective amount" of a composition is an amount necessary or sufficient to achieve the desired result or clinical outcome. For example, the desired result or clinical outcome can be an improvement, prevention, or reduction of a particular disease state. The therapeutic effect contemplated by the embodiments herein includes medically therapeutic, cosmetically therapeutic and/or prophylactic treatment, as appropriate. The specific dose of a compound administered according to embodiments of the present invention to obtain therapeutic effects will, of course, be determined by the particular circumstances surrounding the case, including, for example, the compound administered, the route of administration, and the condition being treated. However, the effective amount administered can be determined by the practitioner or manufacturer or patient in light of the relevant circumstances including the condition to be treated, the choice of compound to be administered, and the chosen route of administration, and therefore, the above dosage ranges are not intended to limit the scope of the invention in any way. A therapeutically effective amount of the compound of embodiments herein is typically an amount such that when it is administered in a physiologically tolerable excipient composition, it is sufficient to achieve an effective systemic concentration or local concentration in or on the tissue to achieve the desired therapeutic or clinical outcome.

As used herein, the term "consists of" or "consisting of" means that the composition or method includes only the elements, steps, or ingredients specifically recited in the particular claimed embodiment or claim.

As used herein, the term "consisting essentially of" or "consists essentially of" means that the composition or method includes only the specified materials or steps and those that do not materially affect the basic and novel characteristics of the claimed invention.

Generally speaking, the term "tissue" refers to any aggregation of similarly specialized cells which are united in the performance of a particular function.

The term "animal" as used herein includes, but is not limited to, humans and non-human vertebrates such as wild, domestic and farm animals.

The term "patient" or "subject" as used herein is an animal, particularly a human, suffering from an unwanted disease or condition that may be treated by the therapeutic and/or compositions described herein.

The term "inhibiting" generally refers to prevention of the onset of the symptoms, alleviating the symptoms, or eliminating the disease, condition or disorder.

"Optional" or "optionally" means that the subsequently described event or circumstance may or may not occur, and that the description includes instances where the event occurs and instances where it does not.

As used herein, "room temperature" means an indoor temperature of from about 20° C. to about 25° C. (68 to 77° F.).

Throughout the specification of the application, various terms are used such as "primary," "secondary," "first," "second," and the like. These terms are words of convenience in order to distinguish between different elements, and such terms are not intended to be limiting as to how the different elements may be utilized.

By "pharmaceutically acceptable," "physiologically tolerable," and grammatical variations thereof, as they refer to compositions, carriers, diluents, and reagents or other ingredients of the formulation, can be used interchangeably and represent that the materials are capable of being administered without the production of undesirable physiological effects such as rash, burning, irritation or other deleterious effects to such a degree as to be intolerable to the recipient thereof.

While the present disclosure is described in detail with reference to GSD Ia, the methods described herein may also be used to treat individuals suffering from other conditions related to steatosis, including, but not limited to, GSD Ib, GSD Ic, NAFLD, NASH, or combinations thereof.

Accordingly, some embodiments in the present disclosure are directed to treating a steatosis-associated disorder, the method comprising administering to a subject in need thereof a therapeutic agent. In some embodiments, the therapeutic agent may be an autophagy-inducing agent of embodiments herein, a lysosomal enzyme of embodiments herein, or a combination thereof. Some embodiments herein are directed to a method of treating GSD I, the method comprising administering to a subject in need thereof a therapeutic agent of embodiments herein. Some embodiments herein are directed to a method of treating GSD Ia, the method comprising administering to a subject in need thereof a therapeutic agent of embodiments herein. Some embodiments herein are directed to a method of treating GSD Ib, the method comprising administering to a subject in need thereof a therapeutic agent of embodiments herein. Some embodiments herein are directed to a method of treating GSD Ic, the method comprising administering to a subject in need thereof a therapeutic agent of embodiments herein. Some embodiments herein are directed to a method of treating NAFLD, the method comprising administering to a subject in need thereof a therapeutic agent of embodiments herein. Some embodiments herein are directed to a method of treating NASH, the method comprising administering to a subject in need thereof a therapeutic agent of embodiments herein.

Some embodiments herein are directed to a method of treating GSD I, the method comprising administering to a subject in need thereof a lysosomal enzyme and an autophagy inducing agent of embodiments herein. Some embodiments herein are directed to a method of treating GSD Ia, the method comprising administering to a subject in need thereof a lysosomal enzyme and an autophagy inducing agent of embodiments herein. Some embodiments herein are directed to a method of treating GSD Ib, the method comprising administering to a subject in need thereof a lysosomal enzyme and an autophagy inducing agent of embodiments herein. Some embodiments herein are directed to a method of treating GSD Ic, the method comprising administering to a subject in need thereof a lysosomal enzyme and an autophagy inducing agent of embodiments herein. Some embodiments herein are directed to a method of treating GSD I, the method comprising administering to a subject in need thereof a lysosomal enzyme and an autophagy inducing agent of embodiments herein, wherein the autophagy inducing agent is not a β2 agonist. Some embodiments herein are directed to a method of treating GSD Ia, the method comprising administering to a subject in need thereof a lysosomal enzyme and an autophagy inducing agent of embodiments herein, wherein the autophagy inducing agent is not a β2 agonist. Some embodiments herein are directed to a method of treating GSD Ib, the method comprising administering to a subject in need thereof a lysosomal enzyme and an autophagy inducing agent of embodiments herein, wherein the autophagy inducing agent is not a β2 agonist. Some embodiments herein are directed to a method of treating GSD Ic, the method comprising administering to a subject in need thereof a lysosomal enzyme and an autophagy inducing agent of embodiments herein, wherein the autophagy inducing agent is not a β2 agonist. Some embodiments herein are directed to a method of treating NAFLD, the method comprising administering to a subject in need thereof a lysosomal enzyme and an autophagy inducing agent of embodiments herein. Some embodiments herein are directed to a method of treating NASH, the method comprising administering to a subject in need thereof a lysosomal enzyme and an autophagy inducing agent of embodiments herein. In some embodiments, the autophagy inducing agent induces autophagy.

GSD Ia is a devastating disease that currently has few treatment options. Although much research has been performed to understand its pathophysiology, no study has been performed linking it to the key cellular process of autophagy. This link not only opens new insights into the pathogenesis and treatment of GSD Ia, but also leads to new potential therapies for a much more common disorder, NAFLD. The development of small molecule therapy for steatosis could provide new agents for NAFLD, which affects >20% of the population in developed countries and >40% of the US adult population.

The therapeutic agents of embodiments herein are believed to manipulate autophagy in GSD I and NAFLD to reverse steatosis in GSD I, NASH, and NAFLD. Autophagy is downregulated in these disorders, and it is believed that stimulating autophagy reverses steatosis. The steatosis of GSD I closely resembles NAFLD, a major unmet health need estimated to affect nearly 40% in the population of the United States. If successful in GSD I, it is believed that modulating autophagy may be effective at reversing steatosis in other conditions such as NAFLD and NASH.

Some embodiments herein are directed to a method of reversing steatosis in a subject in need thereof, the method comprising administering to the subject a therapeutic agent of embodiments herein. Some embodiments herein are directed to a method of reversing glycogen storage in a subject in need thereof, the method comprising administering to the subject a therapeutic agent of embodiments herein. Some embodiments herein are directed to a method of modulating autophagy in a subject in need thereof, the method comprising administering to the subject a therapeutic agent of embodiments herein. Some embodiments herein are directed to a method of inducing autophagy in a subject in need thereof, the method comprising administering to the subject a therapeutic agent of embodiments herein. Some embodiments herein are directed to a method of reducing hepatosteatosis in a subject in need thereof, the method comprising administering to the subject a therapeutic agent of embodiments herein. Some embodiments are directed to treating hepatosteatosis in a subject in need thereof, the method comprising administering to the subject a therapeutic agent of embodiments herein.

In some embodiments, the autophagy-inducing agent may be selected from a thyroid hormone, a mTOR inhibitor, caffeine (trimethylxanthine), a steroid hormone, a PPAR-α agonist, an AMPK activator, a β2 agonist, a calcium channel blocker, a chemical chaperone, an intracellular inositol reducer, a Sirtuin-1 activator, a samesoid X receptor suppressor, or a combination thereof. In some embodiments, the steroid hormone may be dehydroepiandrosterone (DHEA). In some embodiments, the mTOR inhibitor may be selected from rapamycin, Torin1, temsirolimus (CCI-779), everolimus (RAD001), and ridaforolimus (AP-23573), Deforolimus (AP23573, MK-8669), mTORC1/mTORC2 dual inhibitor (e.g. PP242 WYE354), mTOR/PI3K dual inhibitor (e.g. PI103 NVP-BEZ235), an analog thereof, or a combination thereof. In some embodiments, the AMPK activator may be selected from 5-Aminoimidazole-4-carboxamide ribonucleotide (AICAR), quercetin, α-lipoic acid, R-lipoic acid, metformin, resveratrol, guanidine, biguanidine, galegine, ginsenoside, curcumin, berberine, epigallocatechin gallate, theaflavin, hispidulin, a salicylate, a prodrug thereof, or a combination thereof. In some embodiments, the PPAR-α agonist may be selected from bezafibrate, genofibrate, ciprofibrate, gemfibrozil, clofibrate, an analog thereof, or a combination thereof. In some embodiments, the thyroid hormone may be selected from thyroxine (T4), triiodothyronine (T3), an analog thereof, or a combination thereof. In some embodiments, the calcium channel blocker may be verapamil. In some embodiments, the chemical chaperone may be trehalose. In some embodiments, the intracellular inositol reducer may be carbamazepine, lithium chloride, or a combination thereof. In some embodiments, the Sirtuin-1 activator may be methylene blue, resveratrol, or a combination thereof. In some embodiments, sarnesoid X receptor suppressor may be mifepristone. In some embodiments, the autophagy-inducing agent induces autophagy. In some embodiments, the autophagy-inducing agent is not a β2 agonist. In some embodiments, the autophagy-inducing agent is a β2 agonist.

β2 agonists are molecules that stimulate the β2-adrenergic receptor. Numerous β2 agonists are known in the art and may be used in the therapeutic methods of the invention. In some embodiments, the β2 agonist used in embodiments herein may be selected from albuterol, arbutamine, bambuterol, befunolol, bitolterol, bromoacetylalprenololmenthane, broxaterol, carbuterol, cimaterol, cirazoline, clenbuterol, clorprenaline, denopamine, dioxethedrine, dopexamine, ephedrine, epinephrine, etafedrine, ethylnorepinephrine, etilefrine, fenoterol, formoterol, hexoprenaline, higenamine, ibopamine, isoetharine, isoproterenol, isoxsuprine, mabuterol, metaproterenol, methoxyphenamine, norepinephrine, nylidrin, oxyfedrine, pirbuterol, prenalterol, procaterol, propranolol, protokylol, quinterenol, ractopamine, reproterol, rimiterol, ritodrine, salmefamol, soterenol, salmeterol, terbutaline, tretoquinol, tulobuterol, xamoterol, zilpaterol, zinterol, or a combination thereof. In some embodiments, β2 agonists used in the disclosed methods do not interact, or show substantially reduced interaction, with β1-adrenergic receptors. In some embodiments, the β2 agonist is a selective β2 agonist. In embodiments, the β2 agonist is clenbuterol, albuterol, fenoterol, formoterol, salmeterol, or a combination thereof. In embodiments, the β2 agonist is clenbuterol. In some embodiments, the β2 agonist induces or promotes autophagy in the subject.

In some embodiments, the therapeutic agent may be a lysosomal enzyme. In some embodiments, the lysosomal enzyme may be selected from glucocerebrosidase, acid alpha-glucosidase (acid alpha-glucosidase or GAA), alpha-galactosidase, alpha-n-acetylgalactosaminidase, acid sphingomyelinase, alpha-iduronidase, or a combination thereof. In some embodiments, the lysosomal enzyme may be acid α-glucosidase. In some embodiments, the acid alpha-glucosidase may be selected from a GAA, recombinant human acid alpha-glucosidase (rhGAA), alglucosidase alfa, neo-rhGAA, reveglucosidase alpha, an rhGAA administered with a chaperone (e.g. 1-deoxynojirimycin (DNJ), α-homonojirimycin, or castanospermine), or a combination thereof. In some embodiments, the steatosis-associated disorder may be selected from GSD I, NAFLD, NASH or a combination thereof. In some embodiments, GSD I may be selected from GSD Ia, GSD Ib, or GSD Ic. In some embodiments, the GSD I is GSD Ia.

Some embodiments are directed to a composition comprising a therapeutic agent of embodiments herein, and pharmaceutically acceptable excipient. In some embodiments, the therapeutic agent may be an autophagy-inducing agent, a lysosomal enzyme, or a combination thereof. Some embodiments are directed to a composition comprising a β2 agonist and an acid alpha-glucosidase. Some embodiments are directed to an adeno-associated virus ("AAV") vector encoding a lysosomal enzyme, such as acid alpha-glucosidase.

According to some embodiments, a method of treating a steatosis-associated disorder comprises administering a therapeutically effective amount of an autophagy-inducing agent. The autophagy-inducing agent may be administered at a dosage of, for example, 0.1 to 100 mg/kg, such as 0.5, 1.0, 1.1, 1.6, 2, 8, 9, 10, 11, 15, 16, 17, 18, 19, 20, 21, 22, 27, 28, 29, 30, 40, 45, 50, 60, 70, 80, 90 or 100 mg/kg per day, or a range between any two of these values. Dosage forms suitable for internal administration may contain from about 0.1-500 milligrams of active ingredient per unit. In these pharmaceutical compositions, the active ingredient may be ordinarily be present in an amount of about 0.5-95% by weight based on the total weight of the composition.

In some embodiments, the autophagy-inducing agent will be administered in a dose of about 80 μg/day to about 160 μg/day. In some embodiments, the autophagy-inducing will be administered in a dose of about 20 μg/day to about 2100 μg/day, about 20 μg/day to about 720 μg/day, about 20 μg/day to about 500 μg/day, about 20 μg/day to about 300 μg/day, about 20 μg/day to about 200 μg/day, about 40 μg/day to about 2100 μg/day, about 40 μg/day to about 720 μg/day, about 40 μg/day to about 500 μg/day, about 40 μg/day to about 300 μg/day, about 40 μg/day to about 200 μg/day, about 80 μg/day to about 2100 μg/day, about 80 μg/day to about 720 μg/day, about 80 μg/day to about 500 μg/day, about 80 μg/day to about 300 μg/day, about 80 μg/day to about 200 μg/day, or a range between any two of these values. In embodiments, the effective amount for a particular individual may be varied (e.g., increased or decreased) over time, depending on the needs of the individual. In some embodiments, the effective amount of clenbuterol is about 80 to 160 μg/day (or 40 to 80 micrograms by mouth twice daily).

In some embodiments, the effective amount of other drugs that enhance autophagy are provided in Table 1.

TABLE 1

| Drug | Source | Dose and method of administration |
|---|---|---|
| α-lipoic acid (AMPK activator) | 100 mg capsules (OTC dietary supplement) | 20 mg/kg PO daily (adult dose 300 mg BID) |
| Metformin (AMPK activator) | 500 mg Glucophage oral tablets, Bristol Meyers Squibb | 10 mg/kg PO BID (adult dose 500 mg BID) |

TABLE 1-continued

| Drug | Source | Dose and method of administration |
|---|---|---|
| Verapamil | 40 mg oral tablets (generic) | 2 mg/kg PO TID (adult dose 80 mg TID) |
| Trehalose | 100% Pure Trehalose, Swanson Ultra (OTC dietary supplement) | 2-10 g PO daily |
| Carbamezipine | 100 mg tablets Tegretol or oral suspension | 10 mg/kg PO daily (adult dose 200 mg BID) |
| Lithium chloride | lithium citrate 300 mg/ 5 ml syrup | 10 mg/kg BID PO (adult dose 900 mg BID) |
| Bezafibrate | Powder from Sigma | 3.3 mg/kg daily (adult dose 200 mg daily) |
| Methylene blue | U.S.P. powder available from chemical supply houses or 65 mg tablets | 0.4-1 mg/kg TID (adult dose 50 mg TID) |
| Resveratrol | Resvantage Canine, Advantage Biosciences 5 mg tablet | 1 mg/kg PO daily (adult dose 20-500 mg daily |
| Mifepristone | 200 mg Mifeprex tablet (Danco laboratories) | 3 mg/kg daily PO (adult dose 100 to 300 mg daily) |

In some embodiments, the autophagy-inducing agent may be administered once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 days, or a range between any two of these values. In some embodiments, the autophagy-inducing agent may be administered at least once every 1, 2, 3, 4, 5, 6, 7, 8, 9, 10, 11, 12, 13, 14, 15, 16, 17, 18, 19, 20 weeks, or a range between any two of these values. In some embodiments, the autophagy-inducing agent may be administered using single or divided doses of every 60, 48, 36, 24, 12, 8, 6, 4, or 2 hours, or a range between any two of these values, or a combination thereof.

For example, in some embodiments, an autophagy-inducing agent may be administered as a single dose at a single time point, or administered to the patient over the span a several hours (e.g., once every hour, once every two hours, once every three hours, etc.) or over the span of several days (e.g., once a day, once every two days, once every three days, etc.).

As known by those of skill in the art, the optimal dosage of autophagy-inducing agents useful in the present disclosure depend on the age, weight, general health, gender, and severity of the steatosis-associated disorder of the individual being treated, as well as route of administration and formulation. A skilled practitioner is able to determine the optimal dose for a particular individual. Additionally, in vitro or in vivo assays may be employed to help to identify optimal dosage ranges, for example, by extrapolation from dose-response curves derived from in vitro or animal model test systems.

Administering of a therapeutic agent useful in the disclosed methods may be performed by any suitable route, including administration by inhalation or insufflation (either through the mouth or the nose) or oral, sublingual, buccal, parenteral, topical, subcutaneous, intraperitoneal, intravenous, intrapleural, intraoccular, intraarterial, rectal administration, or within/on implants, e.g., matrices such as collagen fibers or protein polymers, via cell bombardment, in osmotic pumps, grafts comprising appropriately transformed cells, etc. In particular, the disclosed therapeutic methods and agents are useful for treating steatosis-associated disorders characterized by severe brain involvement without the need for invasive administration techniques directly to brain (e.g., intrathecal administration).

A therapeutic agent may be administered to the patient as a pharmaceutical composition comprising the therapeutic agent and a pharmaceutically acceptable carrier or excipient. The preparation of a pharmacological composition that contains active ingredients dissolved or dispersed therein is well understood in the art. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent. Among the acceptable vehicles and solvents that may be employed are water, Ringer's solution and isotonic sodium chloride solution. In addition, solid forms suitable for solution, or suspensions, in liquid prior to use can also be prepared. Formulation also varies according to the route of administration selected (e.g., solution, emulsion, capsule).

Pharmaceutically acceptable carriers can include inert ingredients which do not interact with the autophagy-inducing agent, lysosomal enzyme and/or other additional therapeutic agents. These carriers include sterile water, salt solutions (e.g., NaCl), physiological saline, bacteriostatic saline (saline containing about 0.9% benzyl alcohol), phosphate-buffered saline, Hank's solution, Ringer's-lactate saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, dextrose, lactose, trehalose, maltose or galactose, magnesium stearate, talc, silicic acid, viscous paraffin, perfume oil, fatty acid esters, hydroxymethylcellulose and polyvinyl pyrolidone, as well as combinations thereof. The compositions may be mixed with auxiliary agents, e.g., lubricants, preservatives, stabilizers, wetting agents, emulsifiers, salts for influencing osmotic pressure, pH buffers, coloring, flavoring and/or aromatic substances and the like which do not deleteriously react with the active compounds. In addition, the compositions of embodiments herein may be lyophilized (and then rehydrated) in the presence of such excipients prior to use.

Standard pharmaceutical formulation techniques as known in the art can be employed, such as those described in Remington's Pharmaceutical Sciences, Mack Publishing Company, Easton, Pa. Methods for encapsulating compositions. The composition can be a liquid solution, suspension, emulsion, tablet, pill, capsule, sustained release formulation, or powder. The composition can also be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose or magnesium carbonate. For example, a composition for intravenous administration typically is a solution in a water-soluble carrier, e.g., sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is administered by injection, an ampule of sterile water for injection or saline can be provided so that the ingredients may be mixed prior to administration.

The therapeutic agent of embodiments herein may be administered as a neutral compound or as a salt or ester. Pharmaceutically acceptable salts include those formed with free amino groups such as those derived from hydrochloric, phosphoric, acetic, oxalic or tartaric acids, and those formed with free carboxyl groups such as those derived from sodium, potassium, ammonium, calcium, ferric hydroxides, isopropylamine, triethylamine, 2-ethylamino ethanol, histidine, and procaine. For instance, salts of compounds containing an amine or other basic group can be obtained by reacting with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Salts of compounds containing a carboxylic acid or other acidic functional group can be prepared by reacting with a suitable base such as a hydroxide base. Salts of acidic functional groups contain a countercation such as sodium or potassium.

The methods of the present disclosure contemplate single as well as multiple administrations, given either simultaneously or over an extended period of time. In embodiments, the therapeutic agent may be administered at regular intervals (i.e., periodically) and on an ongoing basis, depending on the nature and extent of effects of the steatosis-associated disorder, and also depending on the outcomes of the treatment. In some embodiments, the therapeutic agent's periodic administrations may be bimonthly, monthly, biweekly, weekly, twice weekly, daily, twice a day, three times a day, or more often a day. Administrative intervals may also be varied, depending on the needs of the patient. Therapeutic regimens may also take into account half-life of the administered therapeutic agents of embodiments herein.

Some embodiments are directed to a method of treating a steatosis-associated disorder comprising administering a composition comprising a therapeutic agent of embodiments herein, and a pharmaceutically acceptable excipient. In some embodiments, the steatosis-associated disorder may be GSD Ia, GSD Ib, GSD Ic, NAFLD, NASH, or a combination thereof. In some embodiments, the therapeutic agent may include a lysosomal enzyme, an autophagy-inducing agent, or a combination thereof. In some embodiments, the autophagy-inducing agent may be administered in combination with (e.g. prior to, after, and/or concurrently with) a lysosomal enzyme. Some embodiments provide for a method of treating a steatosis-associated disorder, the method comprising administering an adjuvant therapy comprising an autophagy-inducing agent of embodiments herein to enhance efficacy of an enzyme replacement therapy. In some embodiments, the enzyme replacement therapy may be administration of a lysosomal enzyme.

In some embodiments, the lysosomal enzyme may be administered to the individual in a form that, when administered, targets tissues such as the tissues affected by the disease (e.g., liver, heart or muscle). In some embodiments, the lysosomal enzyme is administered in its precursor form. In some embodiments, a mature form of the lysosomal enzyme (e.g. GAA) that has been modified to contain motifs to allow efficient uptake of the lysosomal enzyme may be administered. In embodiments, the lysosomal enzyme may be selected from glucocerebrosidase, alpha-glucosidase (e.g., acid alpha-glucosidase), alpha-galactosidase (e.g., alpha-gal, alpha-galactosidase or alpha-gal), alpha-n-acetyl-galactosaminidase, acid sphingomyelinase, and alpha-iduronidase.

In some embodiments, a method of treating a steatosis-associated disorder of embodiments herein comprises administering a lysosomal enzyme. In some embodiments, a method of treating a steatosis-associated disorder of embodiments herein comprises administering a lysosomal enzyme and an autophagy-inducing agent. In some embodiments, a method of treating a steatosis-associated disorder of embodiments herein comprises administering an autophagy-inducing agent as an adjunctive therapy to lysosomal enzyme replacement therapy.

In some embodiments, the lysosomal enzyme is acid alpha-glucosidase (GAA). In some embodiments, the GAA is recombinant GAA. In some embodiments, the GAA is a precursor form of recombinant human GAA (rhGAA). In some embodiments, the GAA is either GAA, rhGAA, alglucosidase alfa, neo-rhGAA (modified recombinant human GAA with synthetic oligosaccharide ligands which is sold by Genzyme Corp.), reveglucosidase alpha (a fusion of IGF-2 and GAA sold by Biomarin Pharmaceuticals, Inc.), ATB200 (an rhGAA with a higher bis-M6P content) that is administered in combination with AT221 (an oral chaperone molecule (e.g. 1-deoxynojirimycin (DNJ), α-homonojirimycin, or castanospermine)) (sold by Amicus Therapeutics, Inc.), or a combination thereof. The rhGAA may be alglucosidase alfa (sold by Genzyme Corp. under the tradename Myozyme® (for infantile onset Pompe disease) and Lumizyme®).

GAA may be obtainable from a variety of sources. In some embodiments, a recombinant human acid α-glucosidase (rhGAA) produced in Chinese hamster ovary (CHO) cell cultures is used. Production of GAA in CHO cells yields a product having glycosylation that allows significant and efficient uptake of GAA in tissues such as heart and muscle. In some embodiments, Myozyme® (alglucosidase alfa from Genzyme Corp.), or other recombinant human GAA, may be used in accordance with the invention.

In embodiments, the GAA may have a specific enzyme activity in the range of about 1.0 to about 8.0 μmol/min/mg protein, about 2.0 to about 8.0 μmol/min/mg protein, about 3.0-8.0 μmol/min/mg protein, about 4.0 to about 8.0 μmol/min/mg protein, about 2.0 to about 3.5 μmol/min/mg protein, about 1.0 to about 3.5 μmol/min/mg protein, about 1.0 to about 5 μmol/min/mg protein, about 2.0 to about 5 μmol/min/mg protein, or a range between any two of these values. In some embodiments, the GAA has a specific enzyme activity of at least about 1.0 μmol/min/mg protein, at least about 2.0 μmol/min/mg protein, at least about 2.5 μmol/min/mg protein, at least about 3.0 μmol/min/mg protein, at least about 3.5 μmol/min/mg protein, at least about 4.0 μmol/min/mg protein, at least about 5.0 μmol/min/mg protein, at least about 6.0 μmol/min/mg protein, at least about 7.0 μmol/min/mg protein, at least about 8.0 μmol/min/mg protein, or a range between any two of these values.

In some embodiments, the lysosomal enzyme may be administered alone, or in compositions or medicaments comprising the lysosomal enzyme, as described herein. In some embodiments, for the treatment of steatosis-associated disorders, an autophagy-inducing agent of embodiments described herein may be administered to a patient in combination with a lysosomal enzyme. In some embodiments, an autophagy-inducing agent and lysosomal enzyme may be components of a single pharmaceutical composition. In some embodiments, an autophagy-inducing agent and lysosomal enzyme may be components of separate pharmaceutical compositions that are mixed together before administration. In some embodiments, the autophagy-inducing agent and lysosomal enzyme may be components of separate pharmaceutical compositions that are administered separately. In some embodiments, the autophagy-inducing agent and the lysosomal enzyme may be administered simultaneously, without mixing (e.g., by delivery of the autophagy-inducing agent on an intravenous line by which the lysosomal enzyme is also administered). In some embodiments, the autophagy-inducing agent may be administered separately (e.g., not admixed), but within a short time frame (e.g., within 24 hours) prior to or subsequent to administration of the lysosomal enzyme. A synergistic effect may support reduced dosing of ERT when used with the autophagy-inducing agent and a reduced dosing of the autophagy-inducing agent.

In embodiments, the lysosomal enzyme may be optionally administered in conjunction with other agents, such as antihistamines or immunosuppressants or other immunotherapeutic agents that counteract anti-lysosomal enzyme antibodies. In embodiments, the lysosomal enzymes may include a human enzyme, recombinant enzyme, wild-type enzyme, synthetic enzyme, or a combination thereof.

In some embodiments, gene therapy may be used. For example, genes encoding the aforesaid lysosomal enzymes, such as acid alpha-glucosidase, may be used. In some embodiments, pro-autophagy genes may be used in gene therapy, for example, genes encoding Adenosine-monophosphate-activated protein kinase ("AMPK") and/or transcription factor EB ("TFEB").

In some embodiments, administration of a lysosomal enzyme may also encompass administration of a functional equivalent of a lysosomal enzyme. A functional equivalent may include a compound different from the lysosomal enzyme that, when administered to the patient, replaces the function of the lysosomal enzyme to treat the lysosomal storage disorder. Such functional equivalents may include mutants, analogs, and derivatives of lysosomal enzymes.

In some embodiments, the compositions may be formulated with a physiologically acceptable carrier or excipient to prepare a pharmaceutical composition. Suitable pharmaceutically acceptable carriers may include, but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations may, if desired, be mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. In some embodiments, a water-soluble carrier suitable for intravenous administration may be used.

The composition or medicament, if desired, may also contain minor amounts of wetting or emulsifying agents, or pH buffering agents. In some embodiments, the composition may be a liquid solution, suspension, emulsion, tablet, pill, capsule, sustained release formulation, or powder. In some embodiments, the composition may also be formulated as a suppository, with traditional binders and carriers such as triglycerides. Oral formulation may include standard carriers such as pharmaceutical grades of mannitol, lactose, starch, magnesium stearate, polyvinyl pyrollidone, sodium saccharine, cellulose, magnesium carbonate, etc.

The composition or medicament can be formulated in accordance with the routine procedures as a pharmaceutical composition adapted for administration to human beings. For example, in some embodiments, a composition for intravenous administration may be a solution in sterile isotonic aqueous buffer. In some embodiments, the composition can also include a solubilizing agent and a local anesthetic to ease pain at the site of the injection. In some embodiments, the ingredients may be supplied either separately or mixed together in unit dosage form, for example, as a dry lyophilized powder or water free concentrate in a hermetically sealed container, such as an ampule or sachette indicating the quantity of active agent. In some embodiments, where the composition is to be administered by infusion, it may be dispensed with an infusion bottle containing sterile pharmaceutical grade water, saline or dextrose/water. In some embodiments, where the composition is administered by injection, an ampule of sterile water for injection or saline can be provided so that the ingredients may be mixed prior to administration.

According to some embodiments, a method of treating a steatosis-associated disorder comprises administering a therapeutically effective amount of a lysosomal enzyme. In some embodiments, the lysosomal enzyme is administered as part of a lysosomal enzyme replacement therapy. In some embodiments, the therapeutically effective amount of the lysosomal enzyme (e.g. GAA) is about 1 mg/kg to about 100 mg/kg, about 1 mg/kg to about 75 mg/kg, about 1 mg/kg to about 60 mg/kg, about 1 mg/kg to about 50 mg/kg, about 1 mg/kg to about 40 mg/kg, about 1 mg/kg to about 30 mg/kg, about 1 mg/kg to about 20 mg/kg, about 5 mg/kg to about 100 mg/kg, about 5 mg/kg to about 75 mg/kg, about 5 mg/kg to about 60 mg/kg, about 5 mg/kg to about 50 mg/kg, about 5 mg/kg to about 40 mg/kg, about 5 mg/kg to about 30 mg/kg, about 5 mg/kg to about 20 mg/kg, about 10 mg/kg to about 100 mg/kg, about 10 mg/kg to about 75 mg/kg, about 10 mg/kg to about 60 mg/kg, about 10 mg/kg to about 50 mg/kg, about 10 mg/kg to about 40 mg/kg, about 10 mg/kg to about 30 mg/kg, about 10 mg/kg to about 20 mg/kg, less than about 100 mg/kg, less than about 75 mg/kg, less than about 60 mg/kg, less than about 50 mg/kg, less than about 40 mg/kg, less than about 30 mg/kg, less than about 25 mg/kg, less than about 20 mg/kg, less than about 15 mg/kg, less than about 10 mg/kg, less than about 5 mg/kg, or a range between any two of these values. In some embodiments, the effective dose for a particular individual may be varied (e.g., increased or decreased) over time, depending on the needs of the individual. For example, in times of physical illness or stress, or if anti-enzyme antibodies become present or increase, or if disease symptoms worsen, the amount may be increased.

In embodiments, a therapeutically effective amount of the lysosomal enzyme (or composition or medicament containing the lysosomal enzyme) may be administered at regular intervals, depending on the nature and extent of the disease's effects, and on an ongoing basis. Administration at a "regular interval," as used herein, indicates that a therapeutically effective amount is administered periodically (as distinguished from a one-time dose). The interval can be determined by standard clinical techniques. In some embodiments, the lysosomal enzyme's periodic administrations may be bimonthly, monthly, biweekly, weekly, twice weekly, daily, twice a day, three times a day, or more often a day. The administration interval for a single individual need not be a fixed interval, but can be varied over time, depending on the needs of the individual. For example, in times of physical illness or stress, if anti-enzyme antibodies become present or increase, or if disease symptoms worsen, the interval between doses may be decreased. In some embodiments, a therapeutically effective amount of the lysosomal enzyme at an amount of about 10 mg/kg body weight may be administered weekly. In some embodiments, a therapeutically effective amount of the lysosomal enzyme at an amount of about 5 mg/kg body weight may administered twice weekly.

In some embodiments, a lysosomal enzyme may be administered once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 days, or a range between any two of these values. In some embodiments, a lysosomal enzyme may be administered at least once every 1, 2, 3, 4, 5, 6, 7, 8, 9, 10, 11, 12, 13, 14, 15, 16, 17, 18, 19, 20 weeks, or a range between any two of these values. In some embodiments, a lysosomal enzyme may be administered using single or divided doses of every 60, 48, 36, 24, 12, 8, 6, 4, or 2 hours, or a range between any two of these values, or a combination thereof. For example, in some embodiments, a lysosomal enzyme, functional equivalent thereof, or gene may be administered once every about one to about two, about two to about three, about three to about four, or about four to about five weeks.

In some embodiments, a therapeutic agent may be periodically administered. In some embodiments, periodic administration of the therapeutic agent may be bimonthly, monthly, biweekly, weekly, twice weekly, daily, twice a day, three times a day, or more often a day. In some embodiments, the therapeutic agent may be administered once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 days, or a range between any two of these values. In some embodiments, the therapeutic agent may be administered at least once every 1, 2, 3, 4, 5, 6, 7, 8, 9, 10, 11, 12, 13, 14, 15, 16, 17, 18, 19, 20 weeks, or a range between any two of these values. In some embodiments, the therapeutic agent may be administered using single or divided doses of every 60, 48, 36, 24, 12, 8, 6, 4, or 2 hours, or a range between any two of these values, or a combination thereof. For example, in some embodiments, the therapeutic agent may be administered once every about one to about two, about two to about three, about three to about four, or about four to about five weeks.

In some embodiments, an autophagy-inducing agent may be administered prior to, or concurrently with, or shortly thereafter, the lysosomal enzyme, functional equivalent thereof or gene encoding such enzyme. In some embodiments, the autophagy-inducing agent may be administered sufficiently prior to administration of the lysosomal enzyme so as to permit modulation (e.g., up-regulation) of the target cell surface receptors to occur, for example, at least about two to about three days, about three to about four days, or about four to about five days before the lysosomal enzyme is administered. For example, in some embodiments, the autophagy-inducing agent may be administered to a patient about 0.25, 0.5, 1, 2, 3, 4, 5, 6, 7, 8, 9, 10, 11 or 12 hours, or 1, 2, 3, 4, 5, 6, 7, 8 days, prior to administration of a lysosomal enzyme or a functional equivalent thereof.

In some embodiments, a lysosomal enzyme may be formulated as neutral or salt forms. Pharmaceutically acceptable salts may include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

In some embodiments, a therapeutic agent (or composition or medicament containing the therapeutic agent) is administered by an appropriate route. The therapeutic agent of embodiments herein may be administered by any suitable route, including administration by inhalation or insufflation (either through the mouth or the nose) or oral, sublingual, buccal, parenteral, topical, subcutaneous, intraperitoneal, intravenous, intrapleural, intraoccular, intraarterial, rectal administration, or within/on implants, e.g., matrices such as collagen fibers or protein polymers, via cell bombardment, in osmotic pumps, grafts comprising appropriately transformed cells, etc. In one embodiment, the therapeutic agent may be administered intravenously. In other embodiments, the therapeutic agent may be administered by direct administration to a target tissue, such as heart or muscle (e.g., intramuscular). In yet another embodiment, the therapeutic agent is administered orally. More than one route can be used concurrently, if desired.

In some aspects of the invention, a therapeutic agent is administered in combination with a second therapeutic agent or treatment, and in such cases, the therapeutic agents or treatments may be administered concurrently or consecutively in either order. For concurrent administration, the therapeutic agents may be formulated as a single composition or as separate compositions. The optimal method and order of administration of the therapeutic agents and a second therapeutic agent or treatment can be ascertained by those skilled in the art using conventional techniques and in view of the information set out herein.

The disclosed combination therapies may elicit a synergistic therapeutic effect, i.e., an effect greater than the sum of their individual effects or therapeutic outcomes. Measurable therapeutic outcomes are described herein. For example, a synergistic therapeutic effect may be an effect of at least about two-fold greater than the therapeutic effect elicited by a single agent, or the sum of the therapeutic effects elicited by the single agents of a given combination, or at least about five-fold greater, or at least about ten-fold greater, or at least about twenty-fold greater, or at least about fifty-fold greater, or at least about one hundred-fold greater. A synergistic therapeutic effect may also be observed as an increase in therapeutic effect of at least 10% compared to the therapeutic effect elicited by a single agent, or the sum of the therapeutic effects elicited by the single agents of a given combination, or at least 20%, or at least 30%, or at least 40%, or at least 50%, or at least 60%, or at least 70%, or at least 80%, or at least 90%, or at least 100%, or more. A synergistic effect is also an effect that permits reduced dosing of the therapeutic agents when they are used in combination.

Where a combination therapy is used, in some embodiments, administration of the autophagy-inducing agent and the lysosomal enzyme can take place once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 days, or at least once every 1, 2, 3, 4, 5, 6, 7, 8, 9, 10, 11, 12, 13, 14, 15, 16, 17, 18, 19 or 20 weeks, any range of two of these values, or any combination thereof, using single or divided doses of every 60, 48, 36, 24, 12, 8, 6, 4, or 2 hours, or any combination thereof.

In some embodiments, the autophagy-inducing agent (e.g. β2 agonist) is administered prior to, or concurrently with, or shortly thereafter, the lysosomal enzyme, functional equivalent thereof or gene encoding such enzyme. In some embodiments, the autophagy-inducing agent may be administered sufficiently prior to administration of the lysosomal enzyme so as to permit modulation (e.g., up-regulation) of the target cell surface receptors to occur, for example, at least two-three, three-four or four-five days before the lysosomal enzyme is administered. For example, in some embodiments, the autophagy-inducing agent may be administered to a patient about 0.25, 0.5, 1, 2, 3, 4, 5, 6, 7, 8, 9, 10, 11 or 12 hours, or 1, 2, 3, 4, 5, 6, 7, 8 days, prior to administration of the lysosomal enzyme, recombinant version thereof, or a functional equivalent thereof.

In some embodiments, the lysosomal enzyme and the autophagy-inducing agent of embodiments herein may be formulated into a composition or medicament for treating the steatosis-associated disorders of embodiments herein. Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. In some embodiments, a water-soluble carrier suitable for intravenous administration is used.

In some embodiments, the composition or medicament, if desired, can also contain minor amounts of wetting or emulsifying agents, or pH buffering agents. The composition can be a liquid solution, suspension, emulsion, tablet, pill, capsule, sustained release formulation, or powder. The composition can also be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

In some embodiments, the composition or medicament may be formulated in accordance with the routine procedures as a pharmaceutical composition adapted for administration to human beings. For example, in some embodiments, a composition for intravenous administration typically is a solution in sterile isotonic aqueous buffer. In some embodiments, the composition may also include a solubilizing agent and a local anesthetic to ease pain at the site of the injection. In some embodiments, the ingredients are supplied either separately or mixed together in unit dosage form, for example, as a dry lyophilized powder or water free concentrate in a hermetically sealed container such as an ampule or sachette indicating the quantity of active agent. In some embodiments, where the composition is to be administered by infusion, the composition can be dispensed with an infusion bottle containing sterile pharmaceutical grade water, saline or dextrose/water. In some embodiments, where the composition is administered by injection, an ampule of sterile water for injection or saline can be provided so that the ingredients may be mixed prior to administration.

While embodiments set forth herein are described in terms of "comprising", all of the foregoing embodiments also include compositions and methods that consist of only the ingredients or steps recited or consist essentially of the ingredients and steps recited, and optionally additional ingredients or steps that do not materially affect the basic and novel properties of the composition or method.

This disclosure and embodiments illustrating the method and materials used may be further understood by reference to the following non-limiting examples.

Example 1: In Vitro Testing of Compounds

The role of autophagy in GSD Ia has been carried out in G6pase-deficient mice. A Western blot analysis for the autophagy marker protein LC3 was performed to ascertain the status of autophagy in G6pase-deficient mice. This analysis took advantage of the fact that Cytosolic LC3 (LC3-I) is lipidated and inserted into the autophagosomal membrane, forming LC3-II when autophagosomes are formed. Thus, the ratio of LC3-II to actin or other housekeeping genes can be used as a marker of autophagy. A decrease in hepatic LC3-II protein was observed in G6Pase-deficient mice (FIG. 1(A)), indicating that loss of G6Pase leads to a down-regulation of autophagy.

Chronic stimulation also may lead regulation of autophagy at the transcriptional level. Accordingly, the levels of key ATG proteins were ascertained. Beclin-1 is a key member of the Class III PI3K complex, which is necessary for initiating autophagy. It was found that there is less Beclin-1 present in the livers of mice deficient in G6Pase (FIG. 1(B)). ATG5, which plays a key role in the elongation of autophagosomal membranes, is also decreased in these mice (FIG. 1(B)). Similar data for ATG5 and Beclin mRNA were observed (data not shown). Thus, besides a decrease in hepatic autophagy in G6pase (−/−) mice, the levels of autophagy proteins were also decreased, suggesting that long-term downregulation of autophagy in GSD Ia may occur via transcriptional mechanisms.

Figure 5:
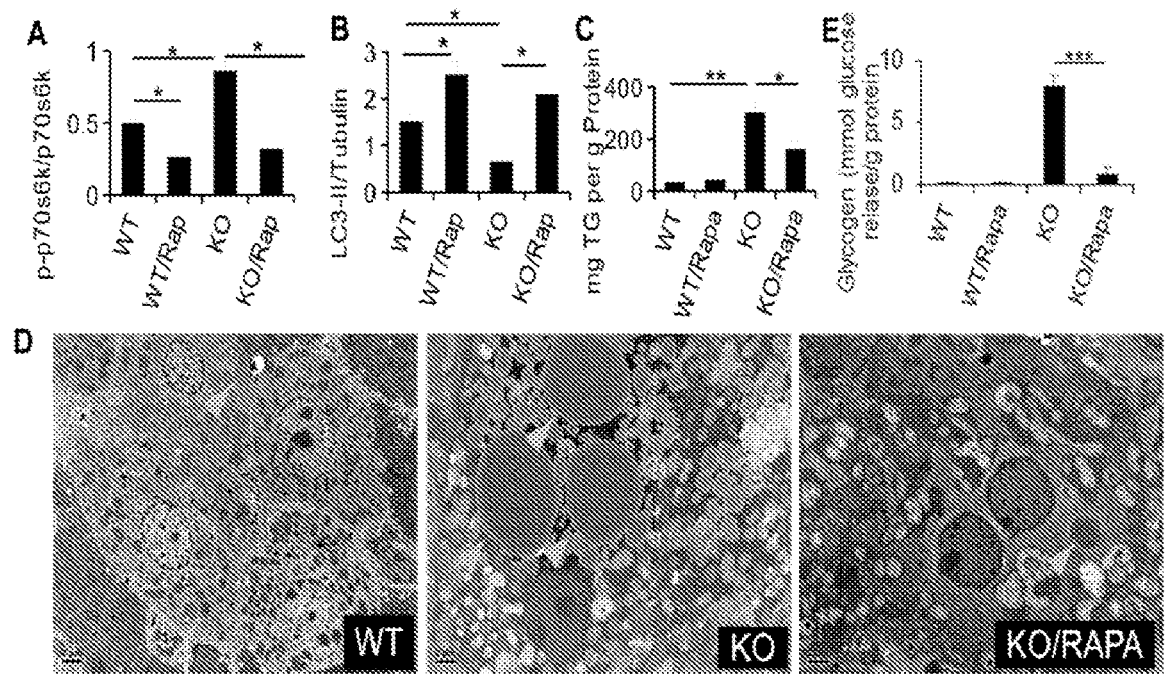
FIG. 5 illustrates that mTORC1 inhibition in GSDIa mice induces autophagy and reduces hepatosteatosis and glycogen storage.
Figure 6:
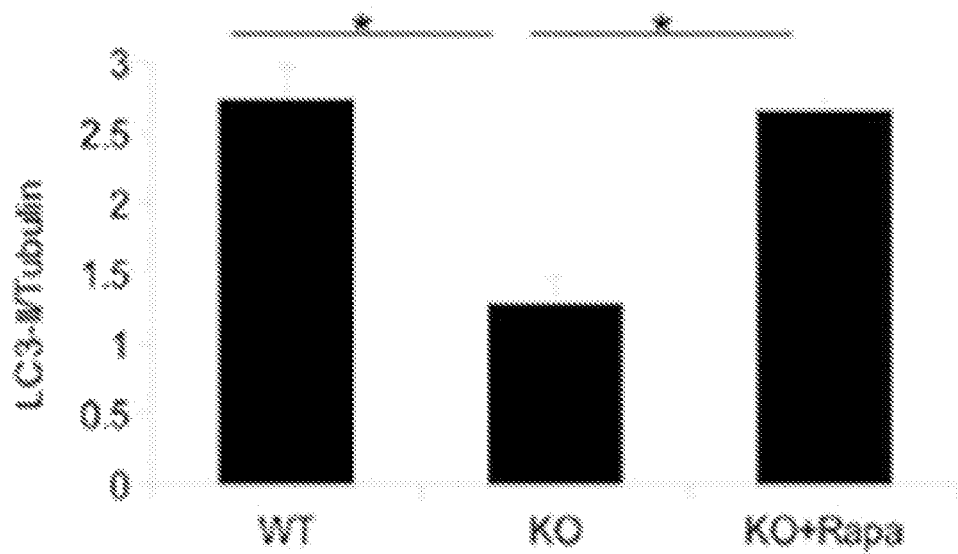
FIG. 6 illustrates the induction of autophagy in kidneys of G6Pase-KO mice. Treatment of G6Pase-KO mice for 1 week with rapamycin increased autophagosome content in the kidney. *=p<0.05.

This data regarding G6Pase deficiency were validated in cell culture studies. AML-12 murine hepatic cells were transfected with siRNA against G6Pase (siG6Pase) for 96 hours to knockdown ("KD") G6Pase, and lipid accumulation and autophagy were assayed. At this time point, LC3-II levels were decreased (FIG. 2(A)). The MTOR and AMPK pathways were investigated to determine which upstream pathways were potentially responsible for the autophagy deficit. Loss of G6Pase led to a decrease in active (phosphorylated) AMPK, as well as a decrease in phosphorylated ACC, its downstream target. Furthermore, an increase in phosphorylated p70s6k, a marker for mTORC1 activity was also noted (FIG. 2(B) and FIG. 3(A)). Both of these changes in cellular signaling are believed to play a role in reducing autophagy. G6Pase-KO mouse livers also showed a decrease in AMPK and an increase in mTOR pathway activities (FIG. 3(B)), suggesting that both pathways may contribute to suppression of autophagy in GSDIa. Furthermore, restoration of AMPK signaling by overexpression of a previously described constitutively active AMPK construct led to restoration of autophagy in G6PC KD cells (FIG. 3(C)). In addition, imaging studies revealed lipid accumulations in siG6Pase-treated AML-12 cells both by fluorescence (FIG. 4(A)) and by electron microscopy (FIG. 4(B)), similar to lipid accumulations present in G6Pase-KO mouse liver (FIG. 5). These results indicate that KD of G6Pase in AML12 cells with siG6Pase can recapitulate the abnormalities of GSD Ia in an in vitro system Candidate drugs for restoring autophagy in the GSD Ia liver were evaluated. Rapamycin is known to both have potent effects on activating autophagy as an mTORC1 inhibitor, and to regulate lipid metabolism due to its effect upon mTORC1. GSD Ia mice were treated with rapamycin daily for 7 days prior to evaluating effects upon autophagy and lipid accumulation in the liver. This Rapamycin treatment decreased phosphorylation of the mTOR substrate p70s6k, a result consistent with inhibition of mTORC1 (FIG. 5(A)). Furthermore, LC3-II was increased (FIG. 5(B)), which is consistent with activation of autophagy, and an equivalent effect was observed in the kidneys of G6Pase-KO mice (FIG. 6). In addition, rapamycin reduced triglycerides in the GSD I liver, suggesting that activation of autophagy could be beneficial in the fatty liver (FIG. 5(C)-5(D)). Importantly, rapamycin reduced glycogen content in the GSDIa liver almost as low as that observed in wild type mouse liver (FIG. 5(E)).

Figure 7:
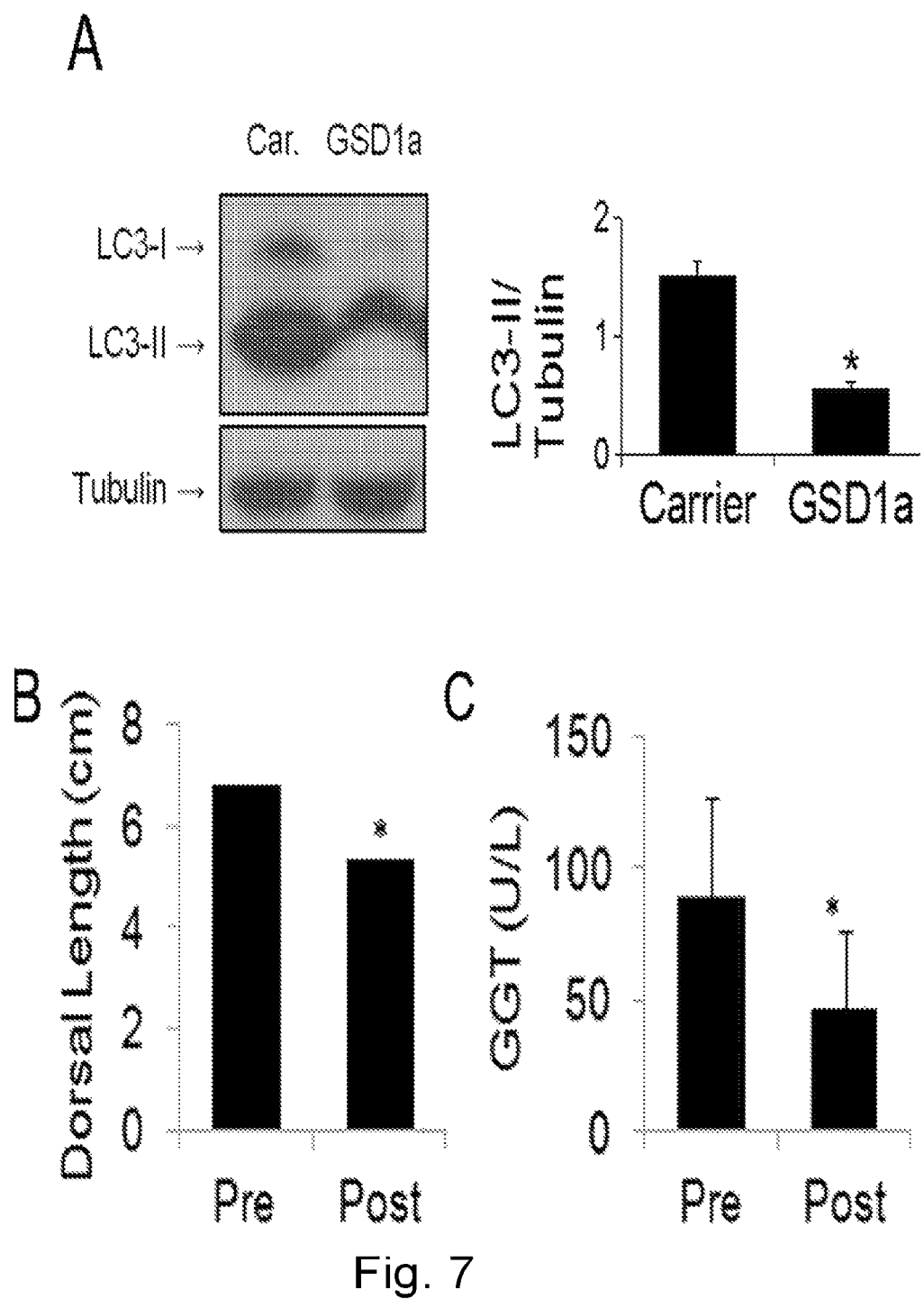
FIG. 7 illustrates that rapamycin treatment to induce autophagy reduced liver involvement in canine GSDIa. Dogs (n=4) were treated with AAV-G6Pase. Rapamycin was administered to induce autophagy (1 mg/kg/day for 1 week).

The effect of rapamycin was further evaluated in dogs with GSDIa that were treated with AAV-G6Pase to promote survival and prevent hypoglycaemia. Dogs with GSDIa had significantly reduced autophagy in the liver, in comparison with unaffected carrier dogs (FIG. 7(A)). Dogs had residual hepatomegaly despite treatment with AAV-G6Pase, which was significantly reduced (FIG. 7(B)) following 1 week of daily oral rapamycin administration (1 mg/kg/day). Serum GGT was significantly decreased (FIG. 7(C)) following rapamycin, indicating reduced hepatocellular damage from GSDIa. These data supported a beneficial effect from stimulating autophagy in the large animal model for GSDIa.

To determine the mechanisms for abnormal autophagy, the cell signaling cascades in the livers of mice lacking functional G6Pase will be studied. The mTORC1 and AMPK pathways will be studied because these pathways are critical for the initiation of autophagy through regulation of phosphorylation of ULK1 protein, a key component of the early autophagasome. It will also be determined how these pathways have been dysregulated in GSD Ia. The effects on the downstream metabolites will also be examined by utilizing the Metabolomics Core Facility at Duke-NUS. The ER stress/UPR pathway, and the function of transcription factors known to induce autophagy, such as the FoxO family, will be investigated. Finally, the abnormalities detected in GSD Ia mouse livers will be evaluated in canine and human GSD Ia livers available under IACUC and IRB approved protocols at Duke University.

In vitro modeling of G6Pase deficiency: To further study the role of autophagy in the pathogenesis of GSD Ia, experiments in cell culture of hepatic cell lines (e.g., AML12) will be performed using both pharmacological and genetic approaches. Experiments using siRNA to knock down (KD) G6Pase in a cell culture model for GSD Ia have begun. Treating hepatic cells with the G6PT inhibitor S4048 may be a better acute model because G6Pase protein is long-lived, leading rapidly to the accumulation of G6P and onset of GSD Ia-like effects in cultured cells. It is possible to probe the acute effects on lipid/glycogen accumulation, autophagy, and upstream signaling pathways over longer periods of time in cell culture. G6Pase will be permanently knocked down in AML-12 cells, which are immortalized mouse hepatocytes that maintain much of the normal hepatic metabolic phenotype, to further examine the chronic effects of the loss of G6Pase on autophagy signaling. This work will allow the understanding how G6P accumulation leads to the derangements in cell signaling and autophagy, and will provide mechanistic insight into potential therapeutic targets. Furthermore, a comparison between the findings in cell culture and in vivo will enable the determination whether the effects of G6Pase knockdown are cell-autonomous, and can be modified by circulating factors or drugs.

TABLE 2

Treating G6pase (−/−) mice with drugs that enhance autophagy

| Drug (class) | Effect |
| --- | --- |
| Bezafibrate (PPAR-α agonists) | Reduced steatosis, increased FAO |
| Caffeine | Increased autophagy, reduced steatosis |
| β2-agonists (clenbuterol) | Increased autophagy in liver (not shown) |
| Rapamycin (mTOR inhibitors) | Increased autophagy in GSDIa liver |
| Thyroid hormone | Increased autophagy, reduced steatosis |
| A-lipoic acid (AMPK activator) | Activated autophagy, reduced intercellular |
| Metformin (AMPK activator) | Activated autophagy, activated AMPK in vitro |
| Verapamil (Calcium channel) | Induced autophagy, reduced cytosolic calcium |
| Trehalose (chemical) | Stimulated autophagy |
| Carbamazepine (Intracellular inositol reduction) | Activated autophagy, reduced hepatosteatosis |
| Lithium Chloride (Intracellular inositol reduction) | Activated autophagy, reduced apoptosis and steatosis |
| Methylene blue (Sirtuin-1 activator) | Activated autophagy, inhibited hepatosteatosis |
| Resveratrol (Sirtuin-1 activator) | Enhanced FAO, reduced |
| Mifepristone (sarnesoid X receptor suppressor) | Activated autophagy, inhibited FXR |

Manipulation of autophagy to investigate efficacy in vitro: Preliminary data has suggested that autophagy is deficient in GSD Ia. Also, findings have suggested that increasing hepatic autophagy may decrease hepatosteatosis and glycogen accumulation. Therefore, autophagy will be artificially induced to determine its therapeutic benefit in GSD Ia. Using the cell culture model generated above, compounds known to induce autophagy in human hepatic cells will be tested. Compounds such as mTOR inhibitors rapamycin, Torin1, and the AMPK activator AICAR, known to have potent effects on autophagy, will be investigated.

It will be examined whether β-oxidation of fatty acids can be increased with inhibition of pmTOR, or with activation of either pAMPK or PPAR-α using appropriate drugs (Table 2). One such drug is bezafibrate (200 µM), a pan-peroxisome proliferator that increased autophagosomes in cultured rat hepatocytes. Fatty acid β-oxidation (FAO) was increased by bezafibrate (400 µM) as indicated by increased carnitine palmitoyl transferase (CPT) activity in cultured cells, and reversed the effects of NAFLD in mice. The FAO/oxidative phosphorylation by metabolomic analysis of acylcarnitines in cell and liver extracts and Seahorse studies of oxygen consumption in vitro will be followed. These studies will enable the identification and understanding of the abilities of known autophagy inducers to improve the metabolic disorder in GSD Ia.

It is believed that G6Pase KD cells will demonstrate the abnormalities of autophagy observed in the G6pase (−/−) mouse liver, namely decreased LC3-II, Atg 5, and Beclin 1. Additionally, it is believed that accumulation of triglycerides will occur following G6Pase in vitro.

Example 2: In Vivo Testing of Compounds in GSD Ia Mice

Figure 8:
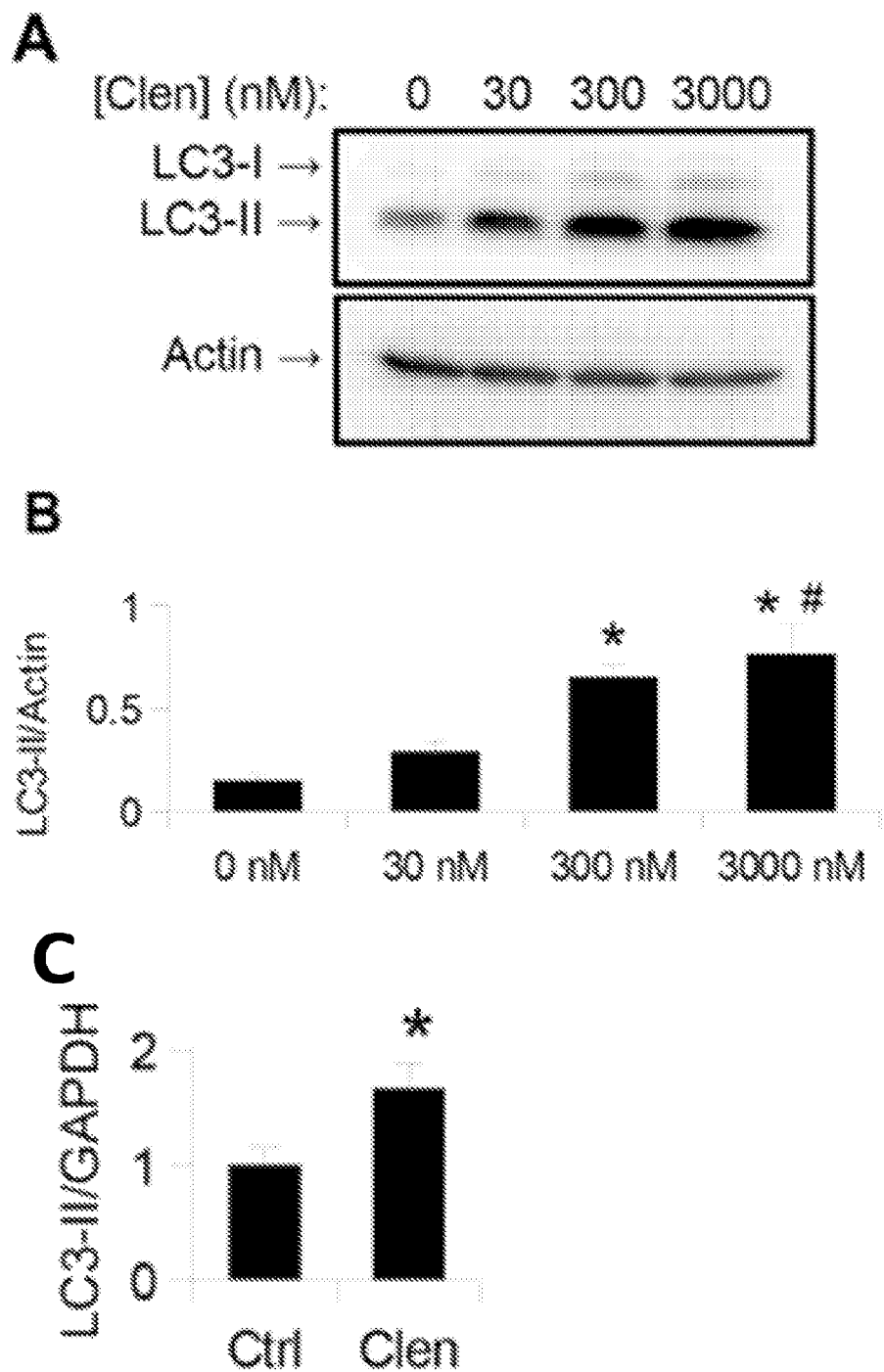
FIG. 8 illustrates that long acting β2-agonist clenbuterol increases autophagosome number in HepG2 cells and in mouse primary hepatocytes.

Clenbuterol was shown to induce autophagy in a murine model for hepatosteatosis (FIG. 8). Increasing concentrations of clenbuterol were capable of activating autophagy as indicated by observing increased LC3-II relative to action (FIG. 8(A)-8(B)), and similarly increased LC3-II was observed in primary hepatocytes (FIG. 8(C)). Thus, clenbuterol, a long-acting β2-agonist with proven safety for long-term treatment of mice, represents a leading candidate among drugs to be considered for the manipulation of autophagy in GSD Ia (Table 1).

The promising autophagy-inducing compounds of Example 1 will be tested in G6Pase (−/−) GSD Ia-model mice to determine their effects on the metabolic derangements of this disease. The mice also will be treated with the autophagy-inducing compound from 5 to 12 days of age. The fasting serum glucose, hepatic lipid and glycogen content, cell signaling pathways, metabolites, as well as hepatic autophagy will be examined. If a compound successfully ameliorates the abnormalities of GSD Ia, the fasting serum glucose should be increased in the treated animals, and the hepatic lipid and glycogen content should be reduced from their abnormally high levels. Thereafter, a successful compound will be evaluated in the high fat diet fed mouse model to evaluate its effects on diet-induced hepatosteatosis in wild-type mice.

Metabolomics provide noninvasive monitoring of therapeutic effects in GSD Ia: Blood and urine sampling will demonstrate the correction of biochemical abnormalities of GSD Ia by metabolomics. At 2, 6, and 12 months of age, mice will be fasted for 8 hours prior to collection of blood for monitoring glucose, which will demonstrate prevention of hypoglycaemia if gluconeogenesis has been increased by small molecule treatment. Metabolomics consisting of plasma acylcarnitines, amino acids, triglycerides, and lactate will be analyzed on fasting samples. GSD-Ia patients have elevated plasma lactate and urinary methylglutaconate, both of which can reflect mitochondrial dysfunction. Urine organic acids will be analyzed for lactate, methylglutaconate, and 3-hydroxybutyric acid by gas chromatography-mass spectrometry as described to detect changes in ketogenesis related to treatment. This panel of testing has revealed unique biomarkers among patients with diabetes, endorsing the selection of these tests for other carbohydrate disorders such as GSD Ia. Metabolomic monitoring will be critical to developing biomarkers to serve as surrogate markers for efficacy in an eventual clinical trial in GSD Ia.

Metabolomic analysis of hepatic extracts will be performed. Acylcarnitine and amino acid profiling will detect any changes related to increased lipolysis and fatty acid beta-oxidation following stimulation of autophagy in mice with hepatosteatosis.

Expected Outcomes: It is believed that elevations of markers for ER stress that are present in the G6pase (−/−) mouse liver will be elevated in G6Pase KD cells. Abnormalities detected in the murine GSD Ia liver should be present in canine and human GSD Ia liver samples, confirming the relevance of these abnormalities to GSD Ia in higher mammals. Effective small molecule therapies will reduce liver triglycerides through increasing autophagy, and the reversal of hepatosteatosis will improve the biochemical abnormalities of GSD Ia.

Metabolomics of blood and urine will reveal the correction of biochemical abnormalities, including hypoglycaemia, lactic acidemia and lactic aciduria, elevated urine ketones, and other biomarkers to be determined. Metabolomics of hepatic extracts will reveal increased long-chain acylcarnitines and decreased amino acids, as demonstrated following stimulation of lipolysis in mice with hepatosteatosis. The small molecule drug will activate autophagy and further normalize the metabolic derangements (particularly lipid) of GSD Ia through metabolomics detection and analyses.

Efficacious compounds will be evaluated in a murine model for NAFLD.

Example 3: Therapeutic Potential of Novel Candidate Drug Therapies in Conjunction with ERT to Correct GAA Deficiency in Mice with Pompe Disease In GAA-KO mice, ERT failed to correct glycogen storage in the skeletal muscle as evidenced by high residual levels of glycogen following standard of care ERT. The ability to directly study novel therapies in engineered human muscle will be of great future utility to Pompe disease research community. Initially, the in vitro human muscle model needs to be correlated with the validated GAA-KO mouse model.

Figure 9:
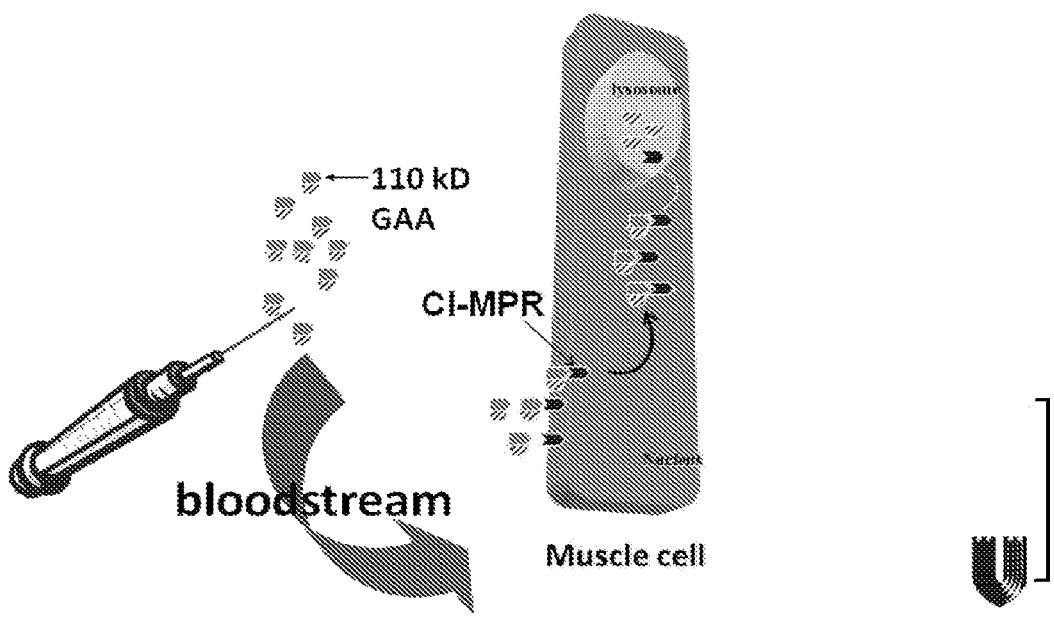
FIG. 9 illustrates that ERT depends upon receptor-mediated uptake of recombinant lysosomal enzymes.
Figure 9:
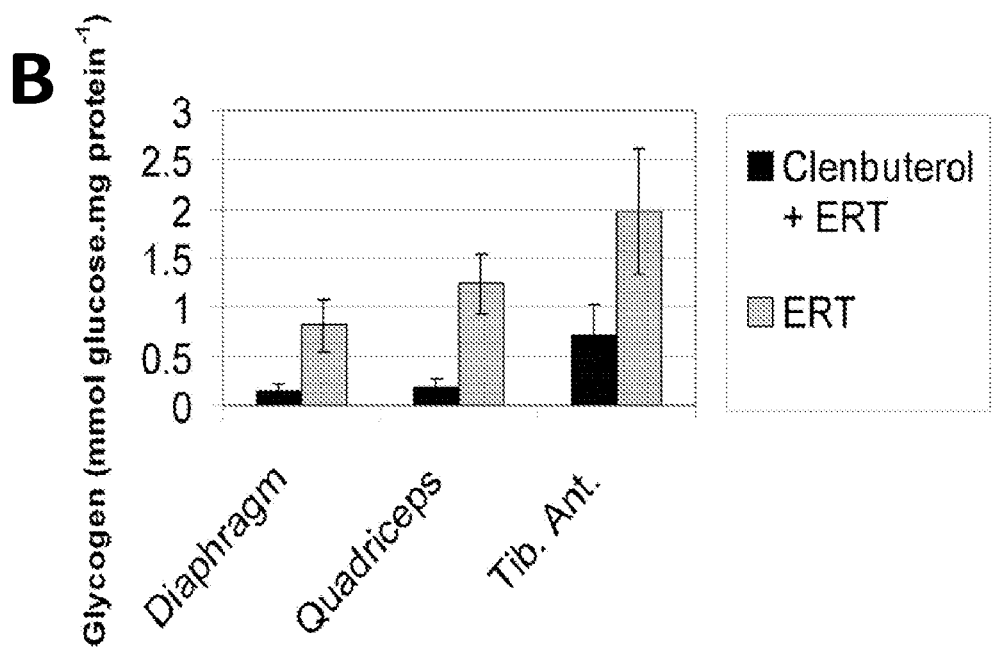

Preliminary Results: Effective dosages for ERT in Pompe disease are up to 100-fold greater than those in other lysosomal disorders. This high-dose requirement has been attributed to the low abundance of cation-independent mannose-6-phosphate receptor (CI-MPR) in skeletal muscle (FIG. 9(A)). The impact of CI-MPR-mediated uptake of recombinant human (rh) acid-α-glucosidase (GAA) upon ERT has been evaluated in GAA knockout (KO) mice with Pompe disease. Clenbuterol, a selective β2 agonist, was revealed to enhance CI-MPR expression and increase efficacy from ERT, thereby demonstrating a key role of CI-MPR with regard to replacement therapy in Pompe disease. The clearance of stored glycogen was increased by β2-agonist treatment during ERT, as demonstrated by lower glycogen content in skeletal muscle following the addition of clenbuterol (FIG. 9(B)) or albuterol treatment. The skeletal muscles comprised primarily of type II myofibers responded more efficaciously to ERT when clenbuterol or albuterol therapy was added, including the tibialis anterior muscle. Type II muscles are resistant to ERT in association with low CI-MPR expression.

The availability of ERT has prolonged the survival of patients, which has increased the understanding of pathology and extent of disease in infantile Pompe disease. Even in patients with a good response to ERT, residual motor weakness (neck flexor weakness, dorsiflexor weakness, mypathic facies, ptosis and strabismus) has been observed. Autopsy of infantile patients has revealed glycogen accumulation in Purkinje cells of the cerebellum, neurons of the cerebral cortex, motor neurons of the spinal cord and in vascular smooth muscle cells of the CNS vasculature, all of which may contribute to the neurological deficits observed in these patients despite compliance with ERT. Correction of neuromuscular involvement and brain pathology has not been possible in Pompe disease, despite adherence to standard-of-care ERT. Our proof-of-concept data demonstrated that adjunctive β2-agonist treatment with ERT reversed neuromuscular involvement in GAA-KO mice. The proposed clinical trial of clenbuterol with ERT will reveal how effectively β2-agonist therapy increases CI-MPR expression and increases receptor-mediated uptake of rhGAA in Pompe disease.

β2-agonist therapy should enhance the response to ERT in Pompe disease and other lysosomal storage disorders. Furthermore, increasing CI-MPR expression should reduce the dosage requirements for ERT or a future gene therapy. Adjunctive therapy with a β2 agonist, such as albuterol, has been shown to improve the 6 minute walk test performance in patients with late-onset Pompe disease. Overall, the availability of treatments that can prove efficacy of ERT for Pompe disease and other lysosomal storage disorders will improve efficacy and reduce the costs of therapies for these diseases.

Protocol: Recombinant human GAA (rhGAA) used in clinical practice will be obtained from Genzyme. Based on our preliminary studies in mice, the impact of adjunctive small molecule therapy upon ERT will be evaluated. Initial doses to be administered are shown in Table 2.

Evaluating the efficacy of alternative small molecule therapy and ERT in GAA-KO mice. ERT is enhanced by the addition of a β2 agonist, clenbuterol, which was demonstrated to induce muscle hypertrophy and to increase the expression of CI-MPR in muscle and to increase the efficacy of ERT. Four other drugs will be administered to groups of GAA-KO mice at the dose anticipated to induce muscle hypertrophy (and increase the expression of CI-MPR, analogous to clenbuterol's effects). These drugs will be administered to groups of 3 month-old GAA-KO mice in drinking water (Table 3). In addition to the three alternative β2 agonists, dehydroepiandrosterone will be tested given its effect upon muscle strength and Igf-1 levels that are analogous to clenbuterol's effects. The dose-response for fenoterol and salmeterol has been equivalent to that for clenbuterol in previous rodent studies. Therefore the same dose for the former two drugs that has been established for clenbuterol will be used when administered in drinking water to mice. Groups of drug-treated GAA-KO mice and mock-treated GAA-KO mice will be analyzed as negative controls (n=8 per group).

TABLE 3

Small molecule therapies to be evaluated in combination with ERT or gene therapy

| Drug | Dose to induce muscle hypertrophy in combination with ERT (reference)[1] |
|---|---|
| Clenbuterol | 30 mg/l |
| Fenoterol | 30 mg/l |
| Formoterol | 4 mg/l |
| Salmeterol | 30 mg/l |
| Dehydroepiandrosterone | 250 mg/l |

[1]Administered in drinking water.

Efficacy will be evaluated by administering biweekly ERT (20 mg/kg rhGAA) to groups of 8 GAA-KO (or DKO) mice (4 male and 4 female). Rotarod testing, wirehang testing, ELISA, and urinary biomarker will be evaluated at 0, 4 and 8 weeks. Tissues will be analyzed at 8 weeks to evaluate (1) GAA activity and glycogen content in the heart, skeletal muscle, and brain; (2) glycogen staining for lysosomal accumulations; (3) Western blot detection of CI-MPR in striated muscles, liver, spleen, and brain; and (4) Western blot detection of hGAA in striated muscles, liver, spleen, and brain. The significance of differences between groups will be tested using a two-sided Wilcoxon rank sum test for continuous variables. A p-value<0.05 will be considered to be statistically significant.

Expected Results: The GAA-KO mice are expected to respond to treatment with the drugs listed in Table 3, because CI-MPR will be increased in skeletal muscle. The efficacy of ERT will be enhanced by the addition of the drugs, increasing biochemical correction and muscle function.

Example 4: Clenbuterol in Conjunction with ERT for GSD Ia

The therapeutic potential of clenbuterol in conjunction with ERT to reverse the glycogen storage and steatosis of GSD Ia will be investigated. Preliminary data revealed that ERT with recombinant human GAA reduced the stored glycogen in the liver of animals with GSD III. The potential of treatment with GAA to reverse glycogen storage in the liver and kidneys of mice with GSD Ia will be evaluated. Adjunctive therapy with clenbuterol will also be evaluated for its efficacy with ERT, because it both reduced hepatosteatosis and increased the uptake of rhGAA in preclinical experiments.

Purpose: These experiments will evaluate the feasibility of ERT with rhGAA for GSD Ia, based upon preliminary data that showed ERT could reduce cytoplasmic stores of glycogen.

Preliminary Results: rhGAA (Myozyme; alglucosidase alfa), an FDA approved therapy for Pompe disease, significantly reduced glycogen levels in primary muscles from patients with GSD Ma. The similarities between GSD Ia and GSD III with regard to accumulations of cytoplasmic glycogen in liver indicate that ERT with rhGAA could be effective in GSD Ia.

Protocol: This experiment will be performed in one week old G6pase (−/−) mice, administering ERT+/−clenbuterol. The fasting serum glucose, hepatic lipid and glycogen content, cell-signaling pathways, metabolites, as well as hepatic autophagy will be examined. If ERT+/−clenbuterol successfully ameliorates the abnormalities of GSD Ia, the fasting serum glucose will be increased in the treated animals, and the hepatic lipid and glycogen content will be reduced from their abnormally high levels.

Expected Results: Following ERT with rhGAA metabolomics of blood and urine will reveal the correction of biochemical abnormalities, including hypoglycaemia, lactic acidemia and lactic aciduria, elevated urine ketones, and other biomarkers to be determined. ERT is anticipated to lower liver and kidney glycogen content, and that adjunctive clenbuterol will increase this effect. Clenbuterol will have two beneficial effects: 1) increasing the receptor-mediated uptake of rhGAA in liver and kidney by upregulating CI-MPR, and 2) increasing autophagy to reduce hepatosteatosis.

Example 5: Phase 1 Clinical Trial Preparation for Candidate Drugs

A pilot clinical trial will be conducted with an adjunctive small molecule therapy showing the greatest promise in the GSD Ia mouse models. A Phase 1 clinical trial with albuterol in patients with Pompe disease has been conducted. The safety of treatment with new small molecule drugs will be evaluated in adult subjects with GSD Ia and Pompe disease. Subjects will start a low dose of drug, and then will be advanced to a higher dose after the 6 week follow-up visit, and will be monitored for 24 weeks.

Plan clinical translation of a new candidate drug for Pompe disease. A Phase I clinical trial of adjunctive drug therapy for late onset Pompe disease is planned. Candidate drug therapy will be combined with ERT during a year-long pilot study. Subjects will return for safety and efficacy monitoring after 6 and 12 weeks of drug therapy, and 12 weeks thereafter. The majority of patients with late-onset Pompe disease have a limited clinical response to ERT, and therefore ERT can be enhanced by upregulating CI-MPR to increase the receptor-mediated uptake of rhGAA. Therapeutic outcomes will be analyzed by comparing the muscle function, pulmonary function, and biochemical correction of muscle in subjects with late-onset Pompe disease treated with ERT, both prior to and during simultaneous β2 agonist therapy.

A clinical trial of new drug therapy in subjects with GSD Ia will be initiated, assessing appropriate clinical endpoints on a similar schedule to the clinical trials in Pompe disease.

Example 6: Use of Rapamycin to Induce Autophagy

The basis for endeavoring to adapt autophagic drug therapies to GSD Ia came from the symptomatic similarities between NAFLD and GSD Ia. NAFLD is characterized by lipid accumulation and hepatomegaly, and in its more severe forms also comprises fibrosis, cirrhosis, and hepatocellular carcinoma. GSD Ia livers likewise present lipid accumulation, hepatomegaly, fibrosis, and eventual hepatocellular carcinoma. Due to the striking similarities of some of the most common symptoms for both diseases and the chronic outcomes, we investigated whether recent advances in autophagy manipulation for NAFLD could be applied to our GSD Ia experimental models.

Figure 10:
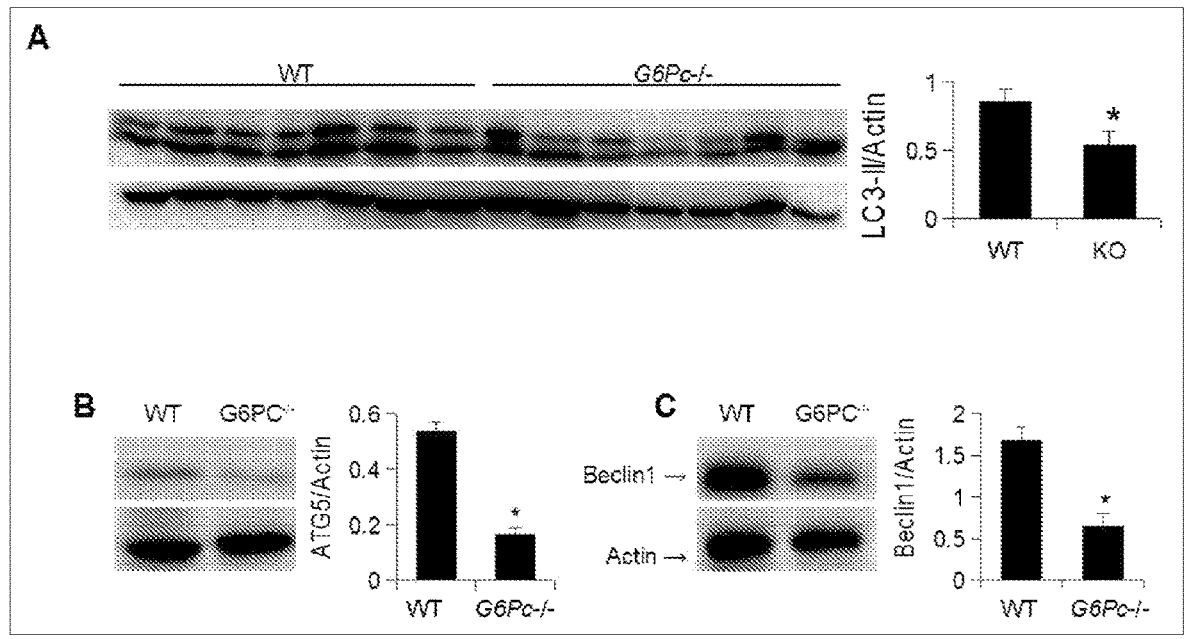
FIG. 10 illustrates loss of G6pc leads to decreased levels of ATG proteins in liver, and decreased levels of autophagosomes in kidney.
Figure 11:
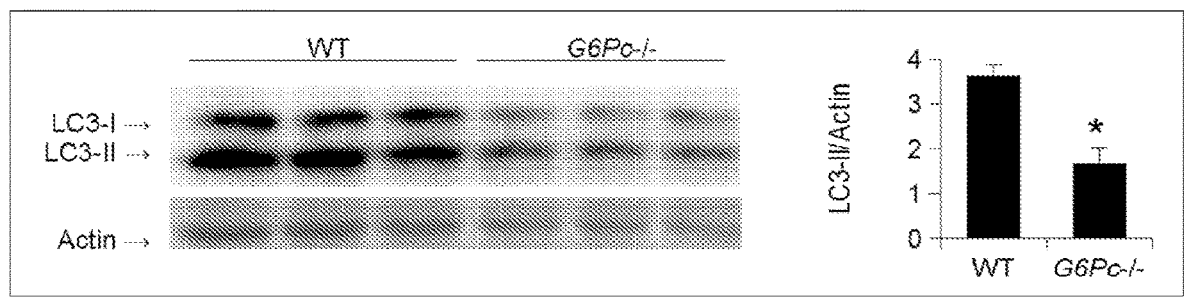
FIG. 11 illustrates LC3-II is reduced in GSD Ia mouse kidneys. Autophagosome number as indicated by LC3-II/actin ratio is decreased in the kidneys of G6pc KO mice. N=3, and * represents p<0.05 between experimental groups. Error bars: SEM.
Figure 12:
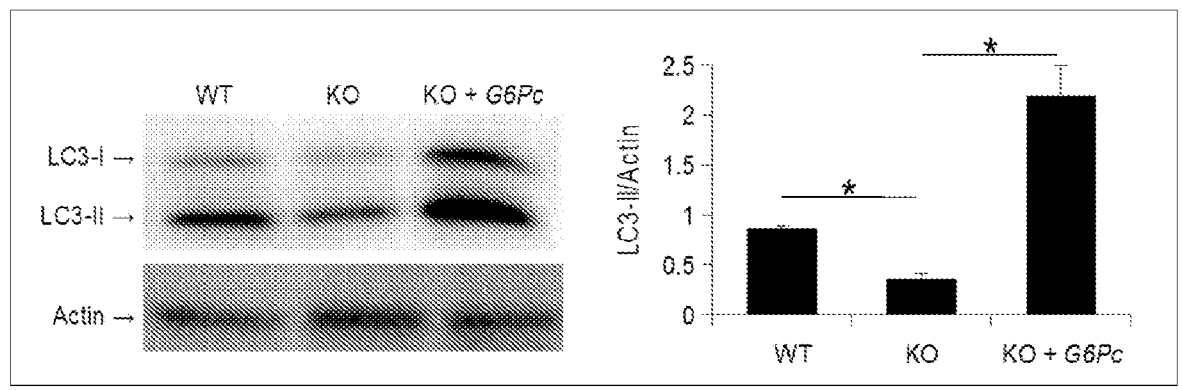
FIG. 12 illustrates AAV-G6Pase treatment prevents reduced autophagy in G6pc−/− mice. Treatment of KO mice with AAV2/9-G6Pase ("+G6Pc") restores autophagy. N=3, and * indicates p<0.05. Error bars: SEM.

First, since LC3-II is known to be diminished in NAFLD, we sought to confirm that it is likewise downregulated in GSD Ia. It was found that GSD Ia mice had reduced levels of LC3-II, a marker of autophagy, as well as reduced levels of the pro-autophagic proteins ATG5 and Beclin 1 (FIG. 10). LC3-II is also reduced in GSD Ia mouse kidneys, the kidney being the secondary organ affected by GSD Ia (FIG. 11). Finally, whether AAV treatment with G6PC transgene-carrying vectors prevents the autophagy deficiency was examined. It was found that providing the therapeutic benefits of a G6PC transgene does indeed reduce development of GSD Ia autophagy-related symptoms from developing (FIG. 12). This demonstrates that autophagy is indeed reduced in GSD Ia mice and is directly caused by G6pc deficiency, showing its relation to NAFLD symptoms and providing more support for our hypothesis that autophagy manipulation, which has benefits in NAFLD models, may provide new treatment routes for GSD Ia models and, eventually, patients.

Figure 13:
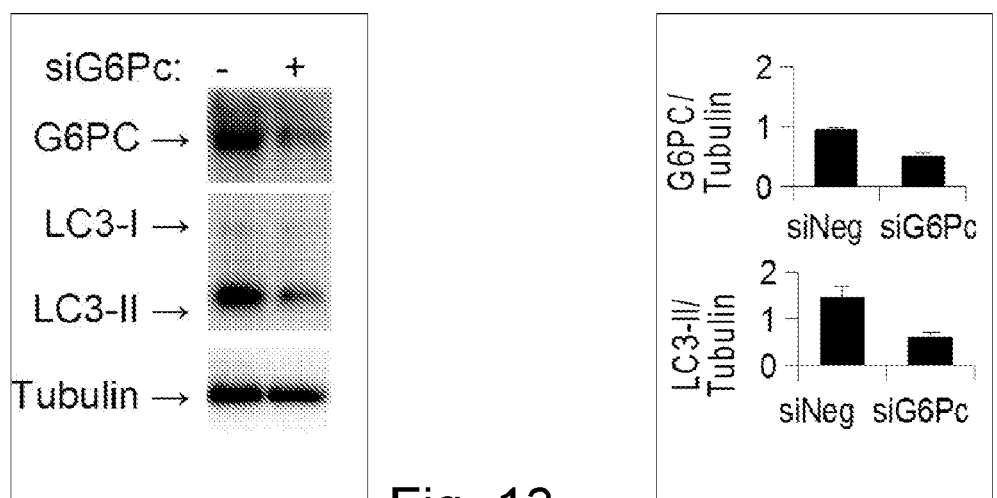
FIG. 13 illustrates LC3-II is reduced in G6pc siRNA-treated AML-12 cells. Treatment of AML-12 mouse hepatocyte cells with siG6pc reduces autophagosome number (LC3-II/tubulin ratio). n=3, and * indicates p<0.05. Error bars: SEM.
Figure 14:
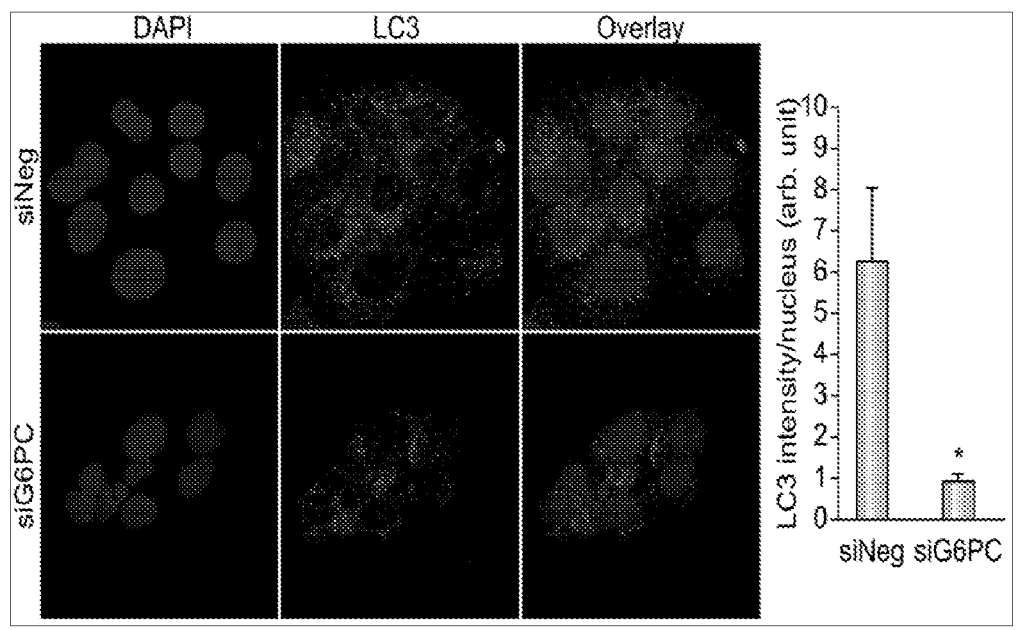
FIG. 14 illustrates G6pc knockdown reduces endogenous LC3 puncta in AML-12 cells stained with α-LC3 antibody. LC3 brightness was quantified and compared to the number of nuclei within the same visual field. n=3 and * indicates p<0.05. Error bars: SEM.
Figure 15:
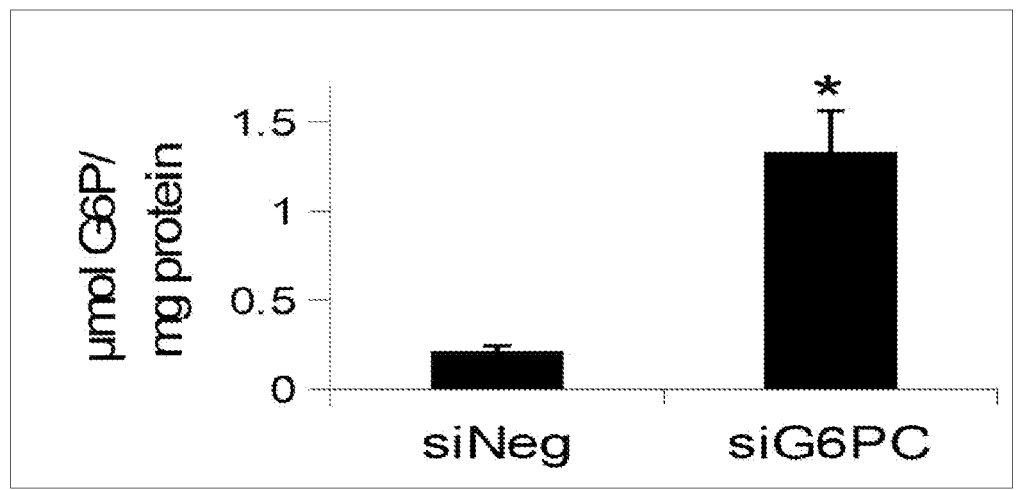
FIG. 15 illustrates glucose-6-phosphate levels are increased in G6pc knockdown AML-12 cells. G6P accumulates in AML-12 cells knocked down for G6pc using siRNA, showing similarity to GSD Ia hepatocytes. n=3, and * represents p<0.05. Error bars: SEM.

Since low-autophagy phenotype of NAFLD occurs in GSD Ia, the potential for autophagy manipulation in GSD Ia was the focus of research. One of these approaches was to recapitulate the GSD Ia phenotype from mouse livers in the AML-12 mouse hepatocyte cell line by knocking down G6pc using siRNA ("siG6P"). The symptoms characteristic of GSD Ia were confirmed in several ways. First, the expected reduction in total LC3-II quantity was confirmed by Western blotting (FIG. 13). To further support this finding, a LC3 puncta staining was performed and the puncta quantified—representing autophagosome formation—per nucleus, and found a corroborative reduction in puncta in knockdown cells (FIG. 14). Since a deficiency in G6PC in humans and animals results in G6P accumulation that feeds into other metabolic pathways and causes disease symptoms, the G6P accumulation in this AML-12 knockdown model was analyzed, and it was found that G6P does in fact accrue when G6pc is knocked down by siRNA in AML-12 cells (FIG. 15).

Figure 16:
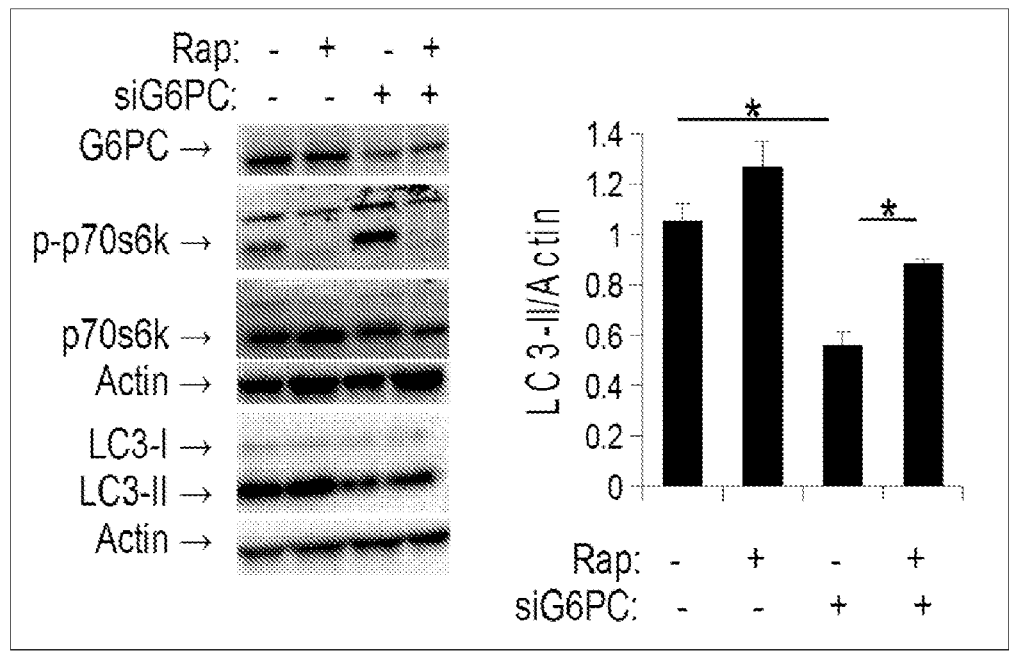
FIG. 16 illustrates rapamycin treatment increases autophagy activity markers in G6pc knockdown AML-12 cells. Western blotting for several autophagy-related proteins indicates that rapamycin (Rap) treatment restores autophagy in G6pc KD AML-12 cells. N=3, * indicates p<0.05 between groups being compared, and ** indicates p<0.01 between groups. Error bars: SEM.
Figure 17:
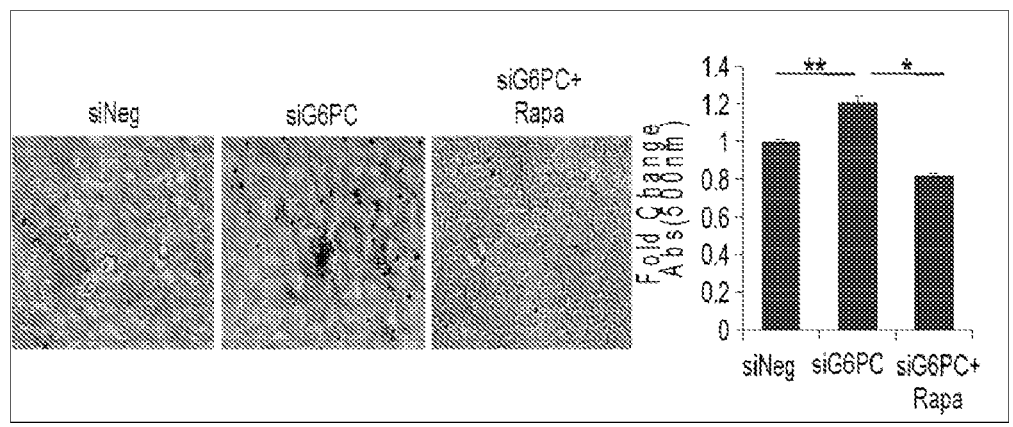
FIG. 17 illustrates rapamycin treatment reduces lipid accumulation in G6pc knockdown AML-12 cells. Oil Red O staining shows that lipid accumulation is restored to low levels by rapamycin application to G6pc knockdown AML-12 cells. N=3, * indicates p<0.05 between groups being compared, and ** indicates p<0.01 between groups. Error bars: SEM.

Having confirmed the autophagy-reduction phenotype in both mice and G6pc siRNA AML-12 cells, the use of rapamycin to induce autophagy in these models was explored. Rapamycin is the prototypical mTOR inhibitor, and since mTOR downregulates autophagy, inhibiting it via rapamycin results in an increase in autophagic activity. This was first tested in the AML-12 model to conserve difficult-to-breed GSD Ia mice. Application of rapamycin to G6pc knockdown AML-12 cells enhanced autophagy and reduced lipid accumulation, as shown in autophagic marker Western blotting and Oil Red O staining (FIGS. 16-17). Phosphorylated p70s6k (p-p70s6k) is indicative of active mTORC, and we observed that rapamycin reduces the amount of p70s6k that is phosphorylated in siG6P-treated AML-12 cells. More importantly, application of rapamycin to knockdown cells results in an increase in LC3-II, which directly indicates an increase in autophagic activity. Similarly, a reduction in lipid accumulation from pro-autophagic rapamycin treatment was expected, and such a lipid reduction, of both visual staining and quantification of Oil Red O adherence intensity was observed.

Figure 18:
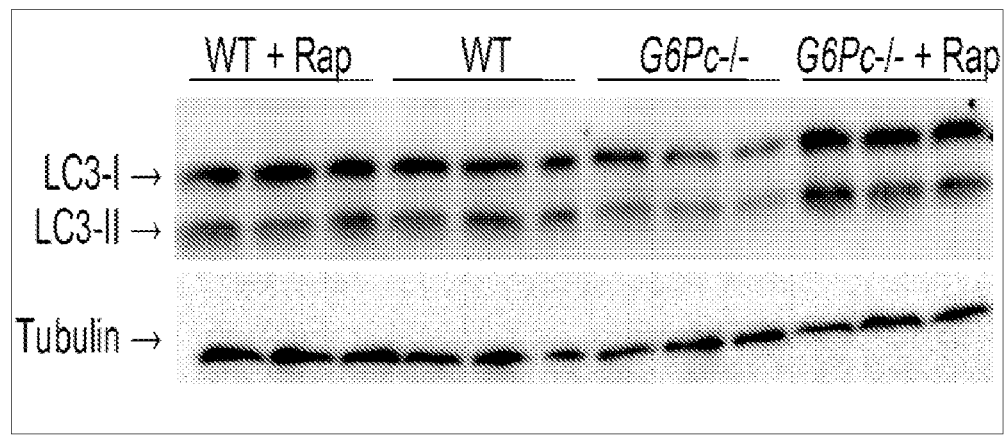
FIG. 18 illustrates Western blotting for LC3-II in mouse livers indicates that treatment of G6pc−/− mice with rapamycin (Rap) increases autophagosome number in the liver (LC3-II/actin). N=3, * indicates p<0.05. Error bars: SEM.
Figure 18:
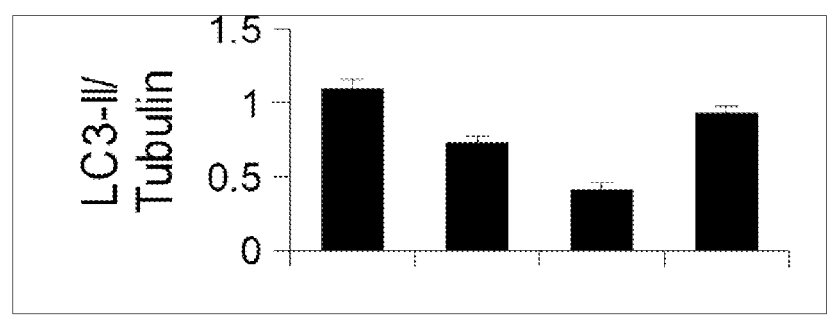
Figure 18:
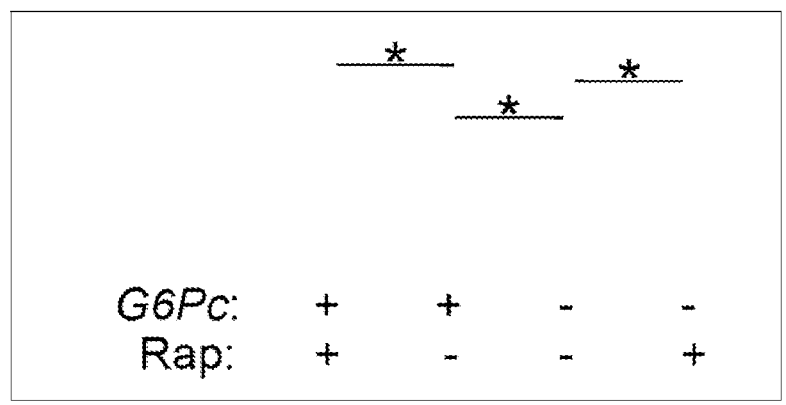
Figure 19:
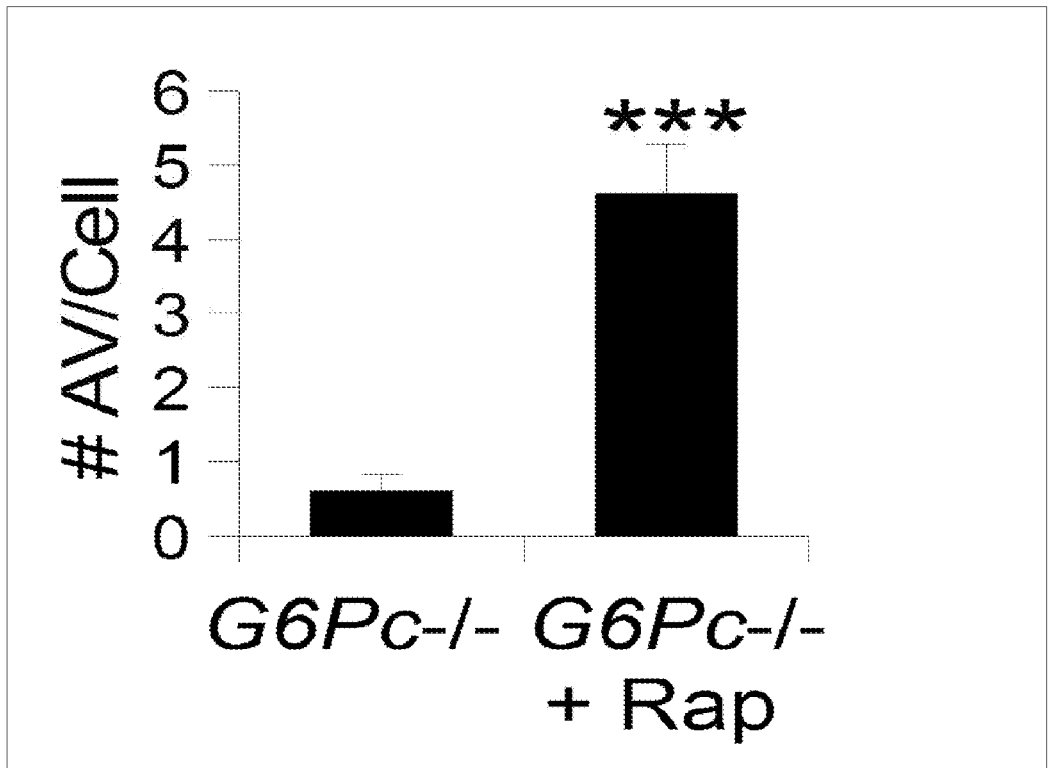
FIG. 19 illustrates ultrastructural electron microscope analysis indicates rapamycin-treated GSD Ia mice showed more hepatic autophagic vesicles than untreated mice. Electron microscope images were analyzed for the presence of autophagic vesicles in GSD Ia mouse hepatocytes without or without rapamycin treatment. N=3, and *** indicates p<0.001. Error bars: SEM.

G6pc–/– mice were given intraperitoneal injections of 5 mg/kg rapamycin suspended in 10% DMSO/90% PBS daily for 7 days starting on day 5 of life. We observed an increase in LC3-II in rapamycin-treated mouse livers via Western blotting as predicted (FIG. 18). Electron microscopy was also performed on mouse livers to quantify autophagic vesicles, and mice treated with rapamycin showed an increase in this indication of autophagy (FIG. 19).

Figure 20:
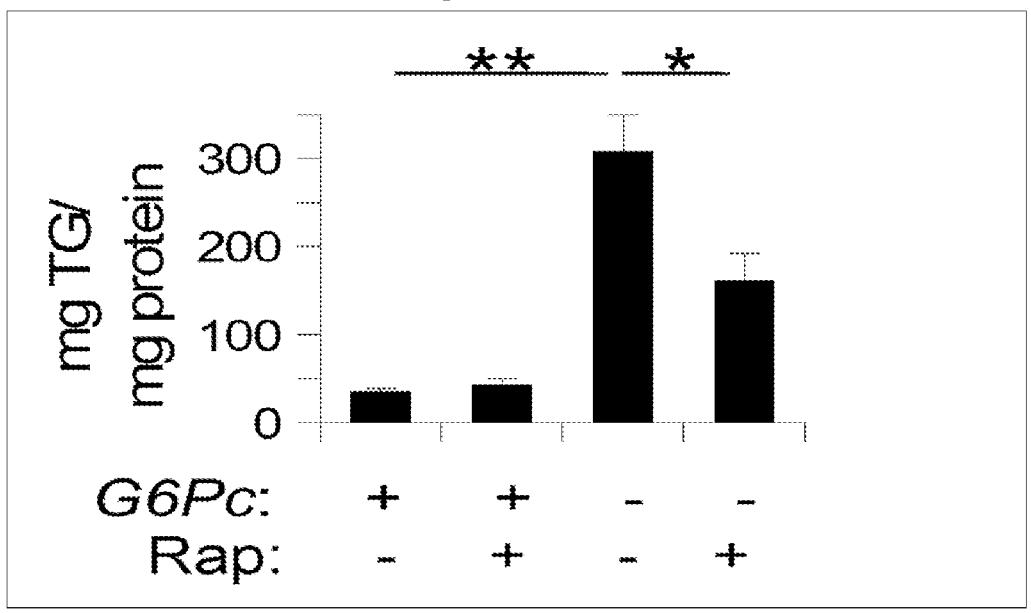
FIG. 20 illustrates rapamycin reduced hepatic triglyceride content in GSD Ia mice. Rapamycin reduced hepatic triglycerides by 50% in GSD Ia mouse livers, which began at 7-fold the levels of wildtype livers. N=4, * indicates p<0.05, and ** indicates p<0.01. Error bars: SEM.
Figure 21:
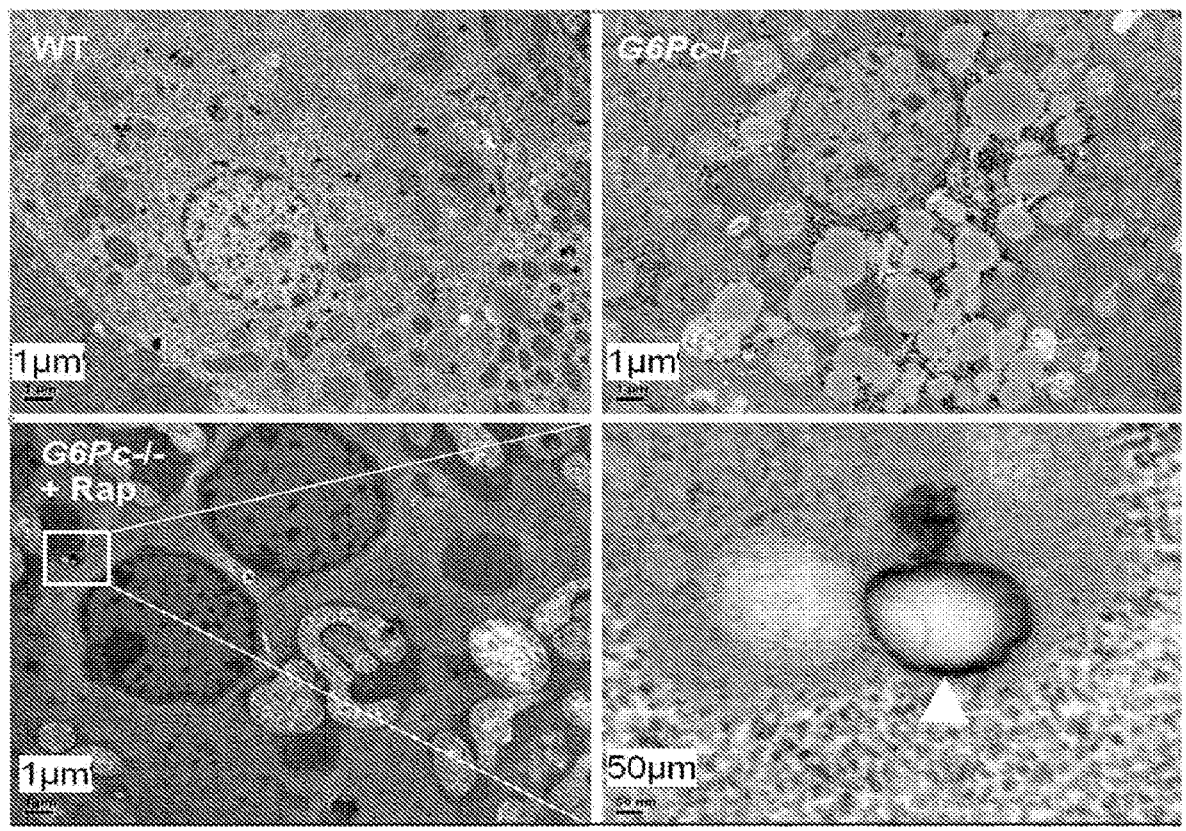
FIG. 21 illustrates lipid vacuoles are diminished in rapamycin-treated GSD Ia mouse livers. Electron microscopy reveals that rapamycin-treated GSD Ia mouse livers have fewer lipid vacuoles in hepatocytes compared with untreated GSD Ia mouse livers.

Liver triglyceride content was quantified in order to determine whether enhancing autophagy reduced lipid accumulation as in AML-12 cells, and we found that liver triglyceride content was indeed reduced by half in G6pc–/– mice following rapamycin administration (FIG. 20). Treatment was sufficient to normalize G6pc–/– mice to the naturally low WT triglyceride levels. That is, the treated group had no significant difference in hepatic triglycerides when compared to vehicle-injected WT mice. Furthermore, electron microscopy revealed a visible reduction in lipid vacuole size and number in GSD Ia mouse livers that received rapamycin (FIG. 21).

Figure 22:
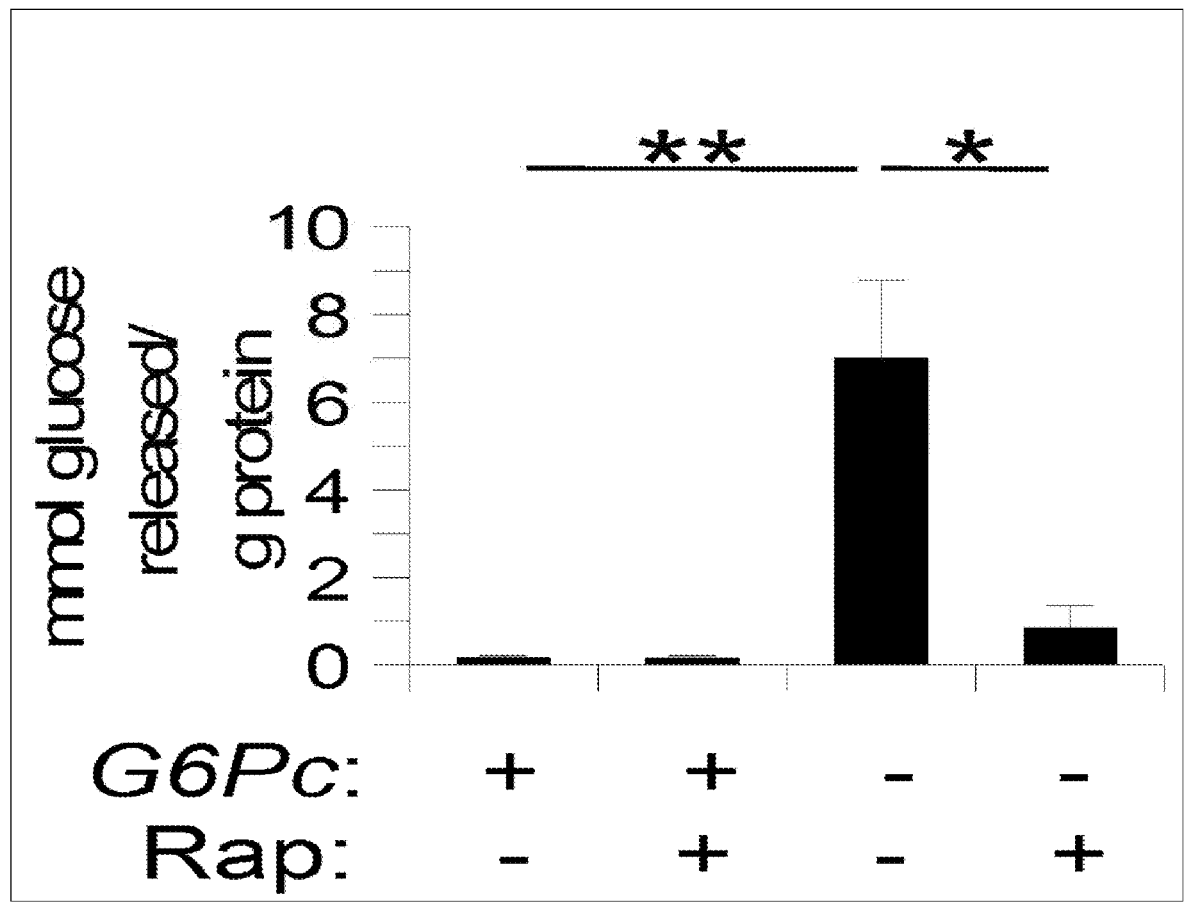
FIG. 22 illustrates liver glycogen accumulation is reduced in GSD Ia mice that receive rapamycin. Glycogen assays revealed a reduction in glycogen (expressed as glucose released during the reaction) in GSD Ia hepatocytes of mice treated with rapamycin compared with those that go untreated. N=5, * indicates p<0.05, and ** indicates p<0.01. Error bars: SEM.
Figure 23:
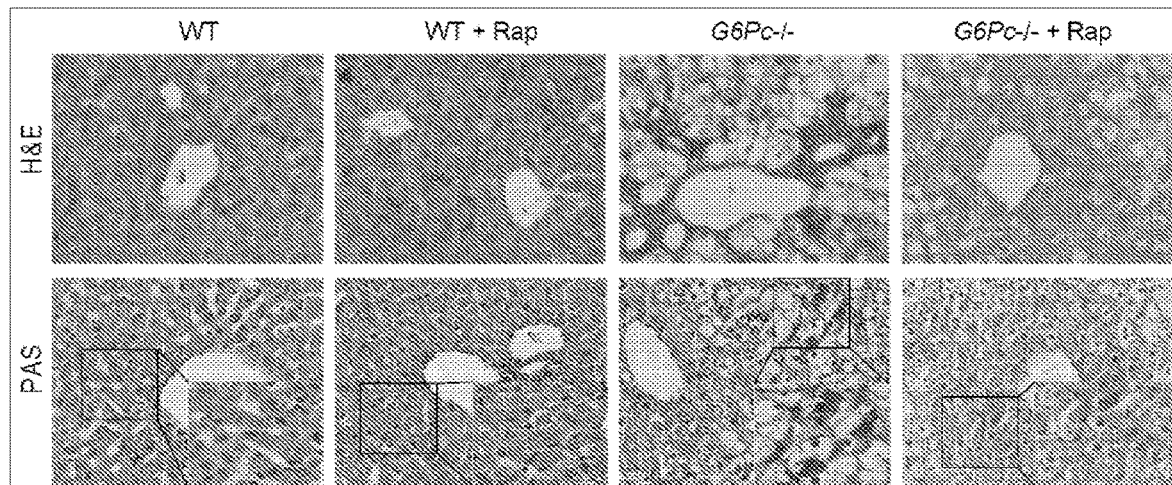
FIG. 23 illustrates histologic analysis (20× magnification) reveals a decrease in lipid and glycogen accumulation in rapamycin-treated mouse livers. Mouse liver sections were stained with H&E and PAS. PAS staining showed reduced heaptic glycogen accumulation in rapamycin-treated mice. H&E stain revealed necrotic cells and lipid vacuoles. In PAS stained samples, insets are digital zoomed 3× further, to 60×.

In addition to autophagy and lipids, hepatic glycogen content was also quantified, the elevation of which is characteristic of GSD Ia, and found a substantial reduction for GSD Ia mice that received rapamycin (FIG. 22). Hepatic glycogen content was further analyzed using PAS staining to stain for polysaccharides, including glycogen, in liver sections. It was found that GSD Ia mice undergoing rapamycin treatment had visibly reduced glycogen-laden vacuoles compared with untreated affected mice (FIG. 23). This confirms our hypothesis that manipulating autophagy can reduce glycogen accumulation by breaking it down through alternate routes from the traditional one relying on G6Pase, bypassing the need for G6Pase in GSD Ia hepatocytes.

Figure 24:
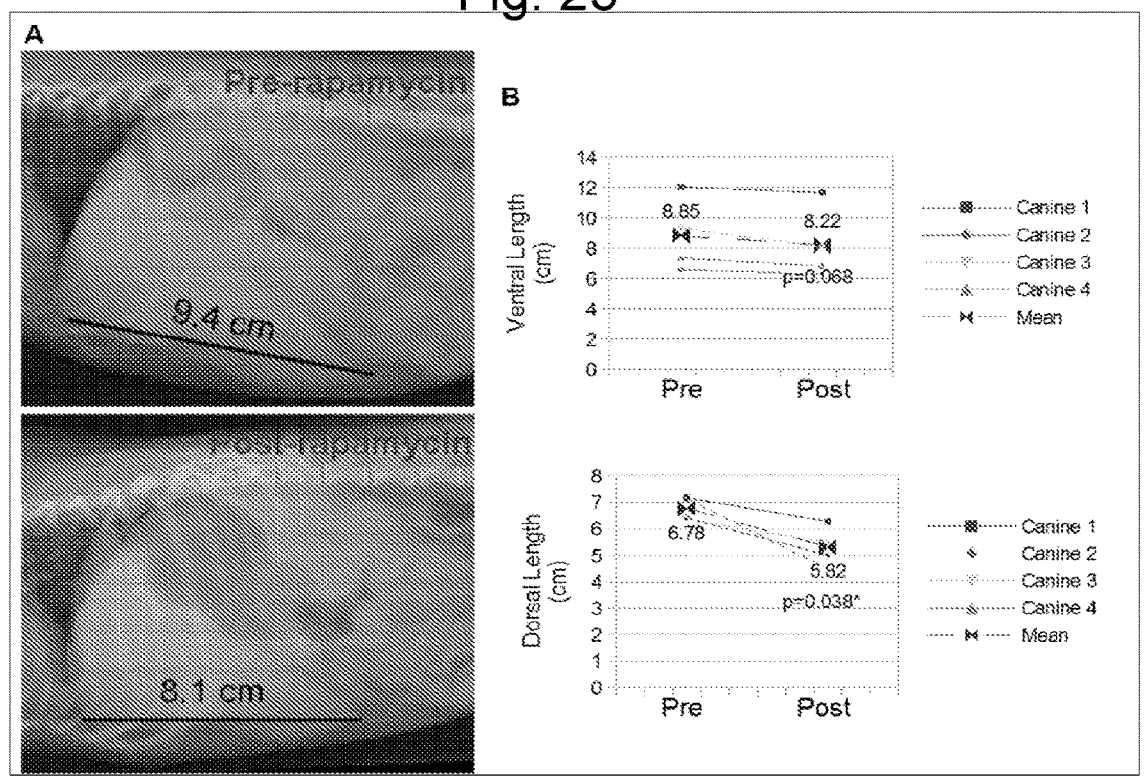
FIG. 24 illustrates treatment of GSD Ia canines with rapamycin reduces hepatic size, and lowers circulating hepatic enzymes.

In addition to the AML-12 and mouse GSD Ia models, we also examined the GSD Ia canine model. The model shows similar symptoms to humans, primarily lethal hypoglycemia, and later in life the canines develop hepatic adenomas and kidney failure like adult human patients. Injections with AAV delivering G6PC to canines are effective for a time, but do not restore 100% of the phenotype. Because treatments are only partially effective, these canines were excellent for examining the efficacy of rapamycin in a large animal model. GSD Ia canines were given 1 mg/kg rapamycin orally daily for 10 days. This was not an endpoint for the canines, so we could not perform the same assays that were done for mice, but we were able to examine liver health using ultrasound to determine the status of the canine's hepatomegaly, and ALT and GGT serum-level assays to determine liver damage. We found that while there was no significant dorsal liver length change, ventral liver length was reduced following rapamycin treatment (FIG. 24). This indicates reduction in hepatomegaly documented prior to drug administration.

Figure 25:
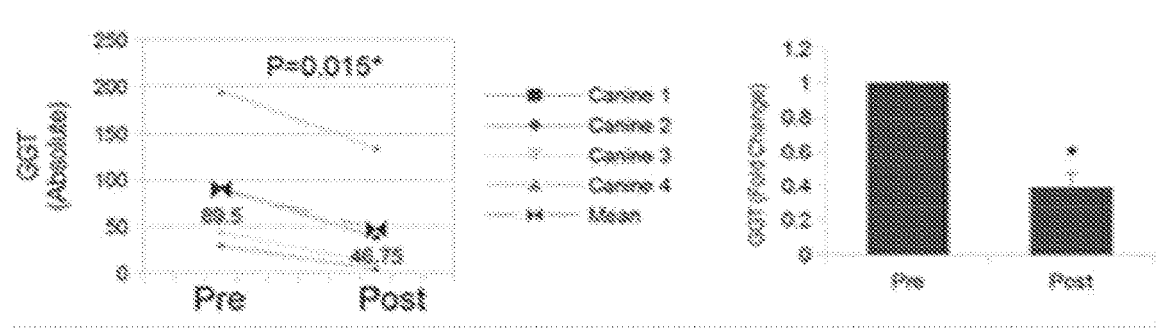
FIG. 25 illustrates GSD Ia canine circulating GGT enzyme levels are reduced following rapamycin treatment. Serum gamma-glutamyl transferase (GGT) levels expressed as absolute and fold-change in the same canines. N=4, and * indicates p<0.05.
Figure 26:
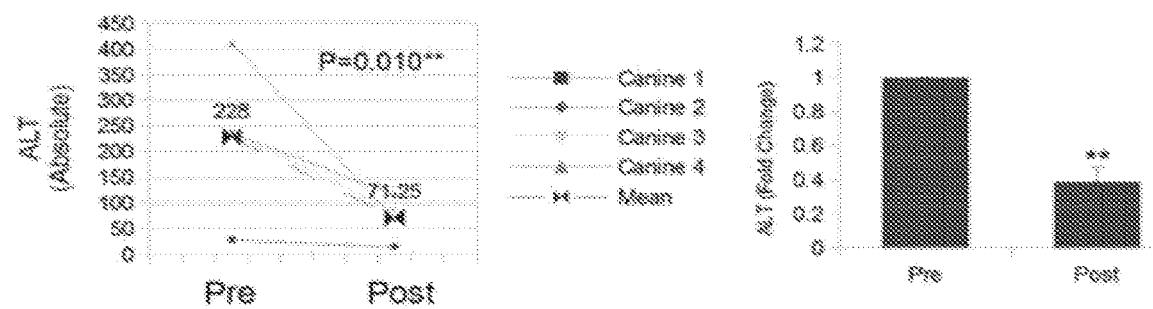
FIG. 26 illustrates GSD Ia canine circulating ALT enzyme levels are reduced following rapamycin treatment. Serum alanine aminotransferase (ALT) levels expressed as absolute and fold-change in the same dogs. N=4, and ** indicates p<0.01. Error bars: SEM.

Likewise, liver health as indicated by serum levels of the liver enzymes GGT and ALT improved with rapamycin administration. GGT levels went down significantly after the 10-day treatment when expressed as either absolute values or fold reduction from the starting point (FIG. 25), and ALT levels went down with significance when expressed as fold reduction from starting values (FIG. 26). These indicate a reduction in liver damage following a 10-day course of oral rapamycin treatment in the canine GSD Ia model.

Example 7: Autophagy-Enhancing Drug Discovery for GSD Ia

The success of the rapamycin experiments at enhancing autophagy and reducing lipid and glycogen accumulation in cells and mice, and improving liver health in canines showed that autophagy modulation could be a powerful new avenue for GSD Ia therapies. However, rapamycin is a potent, nonspecific mTOR inhibitor, causing it to carry many undesirable side effects. We therefore examined several other drugs for their potential in enhancing autophagy in GSD Ia. A literature review turned up 11 drugs that showed promise in other models where autophagy enhancement ameliorates disease symptoms (Table 4). In brief, a wide array of drugs was selected, including those that modulate autophagy via the inositol-3-phosphate (IP3) pathway, those that do so through AMPK modulation to act through mTORC1, and those using yet-undetermined pathways. Analysis of additional literature led to the selection of three concentrations of each compound to be tested in cell culture using the G6pc siRNA knockdown AML-12 mouse hepatocyte cell line model of GSD Ia as an initial screen for the drugs.

TABLE 4

Autophagy-enhancing drugs

| Drug | Published Concentration | Low Conc. | Med Conc. | High Conc. |
| --- | --- | --- | --- | --- |
| a-lipoic acid | 25, 50, 100, 200 µM | 50 µM | 100 µM | 250 µM |
| a-tocopherol | 100, 200, 400, 800 µM | 100 µM | 250 µM | 400 µM |
| Bezafibrate | 100 µM | 25 µM | 100 µM | 250 µM |
| Carbamazepine | Cerebrospinal fluid: 0.7-1.5 µg/mL | 1 µg/mL | 5 µg/mL | 10 µg/mL |
| Lithium | 2, 4, 6, 8, 10, 12 mM[141] Serum: 0.8-1.2 mM | 0.5 mM | 1 mM | 2 mM |
| Metformin | 50 uM, 0.25 mM, 0.5 mM, 2 mM, 2.5 mM | 0.25 mM | 1.5 mM | 2.5 mM |
| Methylene blue | 10, 100, 1000 nM | 10 nM | 100 nM | 1000 nM |
| Mifepristone | 0.1, 1, 10 µM | 0.1 µM | 1 µM | 10 µM |
| Resveratrol | 50, 100 µM | 25 µM | 50 µM | 100 µM |
| Trehalose | 100 mM | 50 mM | 100 mM | 200 mM |
| Verapamil | 70 µM | 50 µM | 100 µM | 250 µM |

Drug concentrations were chosen based on similarity to published concentrations in either cell culture models resulting in target effects or autophagy, or in vivo extracellular fluid concentrations following animal treatments. The latter case is noted with the fluid type. Concentrations used in our in vitro AML-12 cell culture treatments are listed as the low, medium, and high concentrations that were screened.

The first test using AML-12 cells was the Oil Red O stain to examine the presence of lipid vacuoles in cells given the treatments. Cell culture wells were each treated with one of the selected doses for each drug and were scored for both reduced lipid accumulation compared with controls, and improved cell survival, since the siRNA knockdown model has high lethality in the AML-12 cells line (Table 5). The screen's results pointed to several drugs as being the best contenders for further research: bezafibrate, carbamazepine, lithium chloride, and mifepristone.

TABLE 5

Lipid reduction scoring of Oil Red O-stained, drug-treated, G6pc knockdown AML-12 cells

| Drug\Dose | Low | Medium | High |
| --- | --- | --- | --- |
| α-Lipoic acid | + | − | 0 |
| α-Tocopherol | 0 (Spotty +) | − (Spotty ++) | − |
| Bezafibrate | − | + | ++ |
| Carbamazepine | +++ | + | 0 |
| Lithium Chloride | +++ | ++ | + |
| Metformin | + | +/++ | 0 |
| Methylene Blue | + | −− | −−− |
| Mifepristone | + | + (Spotty ++) | ++ (Great survival) |
| Trehalose | + | −− | − (High death) |
| Verapamil | − | + (But high death) | −− (Very high death) |
| Rapamycin | −− | −− | −−− |
| Resveratrol | + | 0 (Spotty ++) | −−− |
| DMSO | − (Spotty +) | −− | −− |
| Ethanol | − | − | −− |

G6pc siRNA knockdown AML-12 cells were given three different doses of each drug treatment. After 72 hours of growth, the media was changed to ketogenic media and appropriate quantities of each drug were added. This was performed in duplicate. Oil Red O staining was then performed and bright field images acquired at 10× magnification.

Drug treatments at three doses each were performed on G6pc siRNA knockdown AML-12 cells. Following oil red O staining the whole plates were evaluated visually for reductions in lipid accumulation. Treatments were performed in duplicate. −/0/+/++/+++ indicates the degree of improvement, or lipid reduction, caused by the treatment, with + indicating positive benefits.

Figure 27:
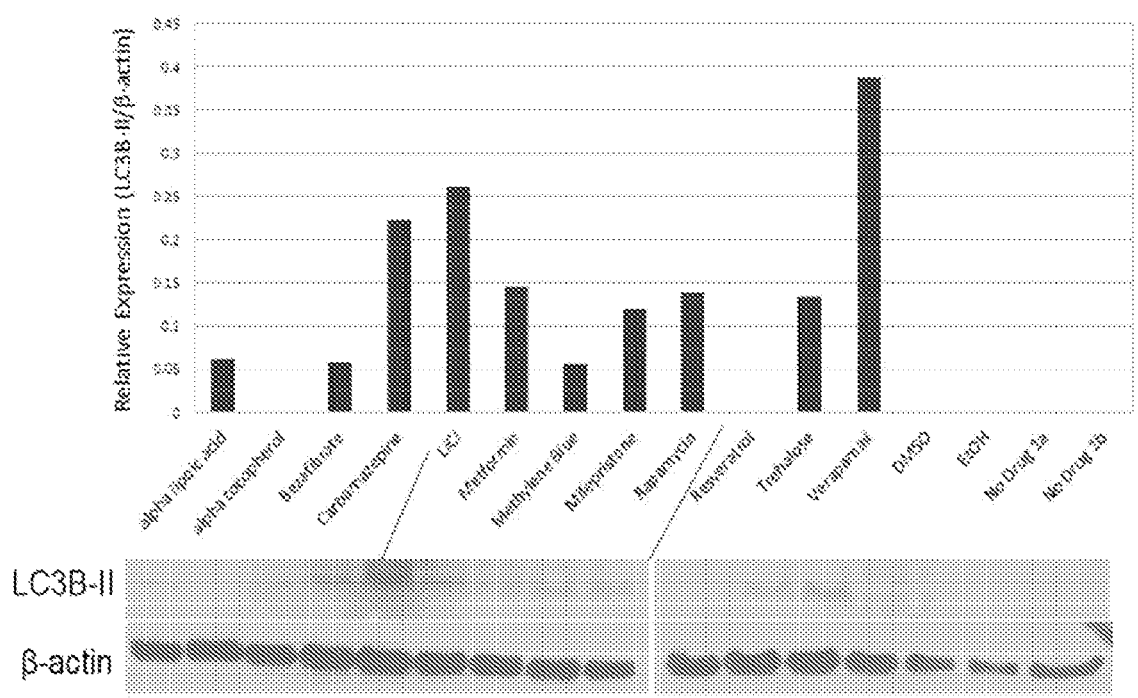
FIG. 27 illustrates LC3 Western blot of drug-treated G6pc knockdown AML-12 cells. Western blotting was performed on AML-12 cells incubated for 24 hours with the described drug conditions. LC3 was quantified and normalized against each condition's β-actin protein quantification.

In addition to Oil Red O staining, cells were analyzed via Western blots for restored LC3 expression for each drug, under the conditions that had optimal effects in the Oil Red O screen (FIG. 27). Since the Western antibody previously used successfully for rapamycin treatment LC3 blots had been discontinued by the manufacturer, we tested two alternative antibodies and chose the one from Cell Signaling Technologies because it gave the strongest signal-to-noise ratio under our experimental conditions. Western blotting confirmed the autophagy-enhancement effects of many drugs that showed lipid reduction through the Oil Red O stain, and in particular it corroborated the results of bezafibrate, carbamazepine, lithium chloride, and mifepristone application by demonstrating the increase in LC3 autophagic marker predicted based on their lipid-reducing effects (FIG. 27).

Western blotting was performed on AML-12 cells incubated for 24 hours with the described drug conditions. LC3 was quantified and normalized against each condition's β-actin protein quantification.

Carbamazepine and lithium have potent psychoactive effects. Lithium compounds were among the first mood-stabilizing drugs used to treat bipolar disorder and schizophrenia circa 1949, and anticonvulsants, particularly carbamazepine, have been combined with lithium in the treatment of bipolar disorder and schizophrenia for over three decades. The fact that lithium is still prescribed as a mood stabilizer in the treatment of bipolar disorder after 75 years stands as a testament to the potency of its psychoactive effects. These beneficial effects for patients suffering from psychiatric illnesses would instead become serious side effects in patients prescribed lithium and/or carbamazepine to ameliorate GSD Ia symptoms, so lithium chloride and carbamazepine have not been pursued in mice as potential GSD Ia treatments at this time.

Mifepristone is used to induce chemical abortions up to day 70 of pregnancy. These on- and off-label purposes could produce significant side-effects in GSD Ia patients using mifepristone to improve their autophagic activity. Furthermore, the side effects of the drug itself as described on the FDA label include nausea, vomiting, and diarrhea, which could make it difficult for patients to intake sufficient calories for combating hypoglycemia, potentially negating the benefits. Therefore, administration of mifepristone was not pursued in GSD Ia mice.

This left bezafibrate as the best candidate to emerge from the screen. Bezafibrate is a PPARα agonist used to lower cholesterol levels and prevent hyperlipidemia to reduce the risk of heart disease. Since hyperlipidemia is a symptom of GSD Ia, this pre-established on-label effect could have benefits in addition to autophagic enhancement in patients. In terms of side effects, bezafibrate does induce loss of appetite and elevation in circulating liver enzymes. While these could complicate therapeutics taking advantage of the medication for GSD Ia, the overall effects on autophagy and hyperlipidemia would likely outweigh the downsides, so we chose bezafibrate to move forward as our best drug candidate in GSD Ia mice.

G6pc−/− knockout mice were administered intraperitoneal injections of bezafibrate 25 mg/kg/day suspended in 10% DMSO/90% PBS IP for 3 days.

Figure 28:
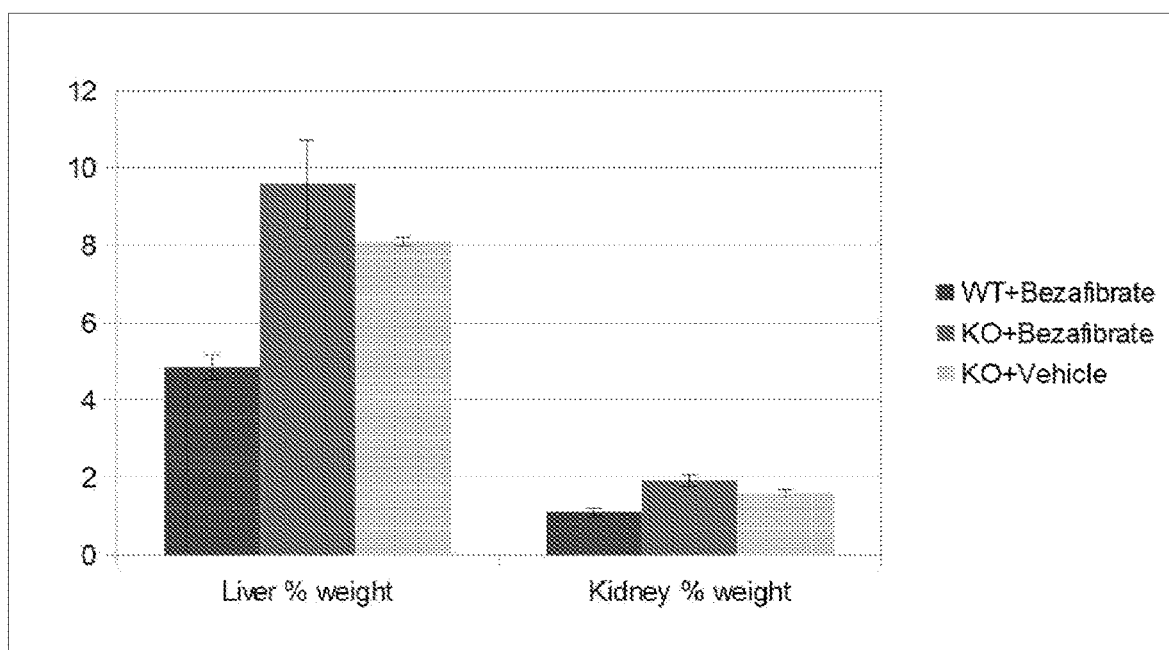
FIG. 28 illustrates bezafibrate-injected GSD Ia mice liver and kidney weights. Livers and kidneys from mice undergoing bezafibrate injections were weighed at the time of collection, weights expressed here as percentage of body weight. * indicates p<0.05. Error bars: mean±SD.

At the time of tissue collection, blood glucose was analyzed and affected mice were found to have no increase when treated with bezafibrate, their levels consistently below the threshold of detection (<20 mg/dL). However, liver and kidney weights were recorded at the time of sacrifice, and these data revealed a slight difference in kidney size as a percentage of body weight. Bezafibrate caused a very small but quantitatively significant increase in kidney weight expressed as a percentage of total body weight (p<0.046) (FIG. 28). This runs contrary to the expectation that bezafibrate would reduce kidney size in G6pc−/− mice.

Livers and kidneys from mice undergoing bezafibrate injections were weighed at the time of collection, weights expressed here as percentage of body weight. * indicates $p<0.05$. Error bars: mean±SD.

Figure 29:
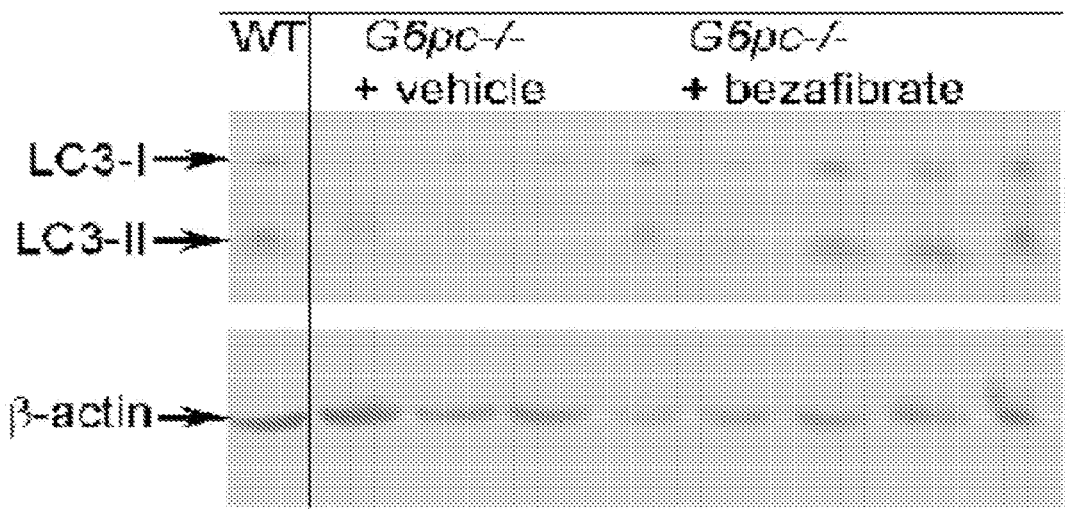
FIG. 29 illustrates treatment of G6Pc−/− mice with bezafibrate increases autophagosome number in the liver. Bezafibrate was administered by intraperitoneal injection to groups of 5 day old mice, and livers were collected 3 days later. Groups: bezafibrate, n=5; vehicle, n=3. (A) Western blots for LC3-II and β-actin. (B) Quantification of LC3-II (LC3-II/β-actin). Mean+/−SD shown. * indicates p<0.05.
Figure 29:
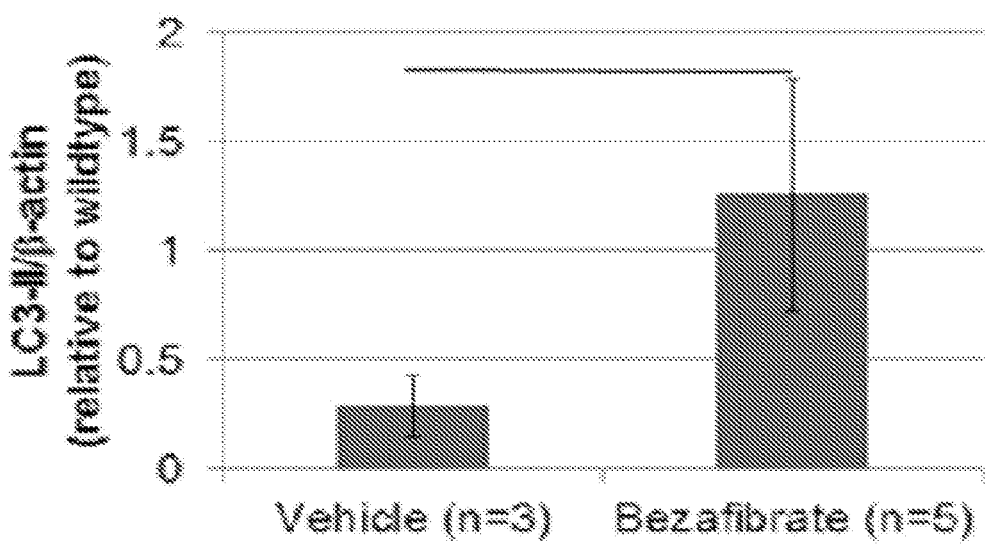

A single administration of bezafibrate increased LC3-II significantly, in comparison with vehicle-treated mice of the same age (FIG. 29). This result demonstrated increased formation of autophagosomes consistent with the induction of autophagy.

Figure 30:
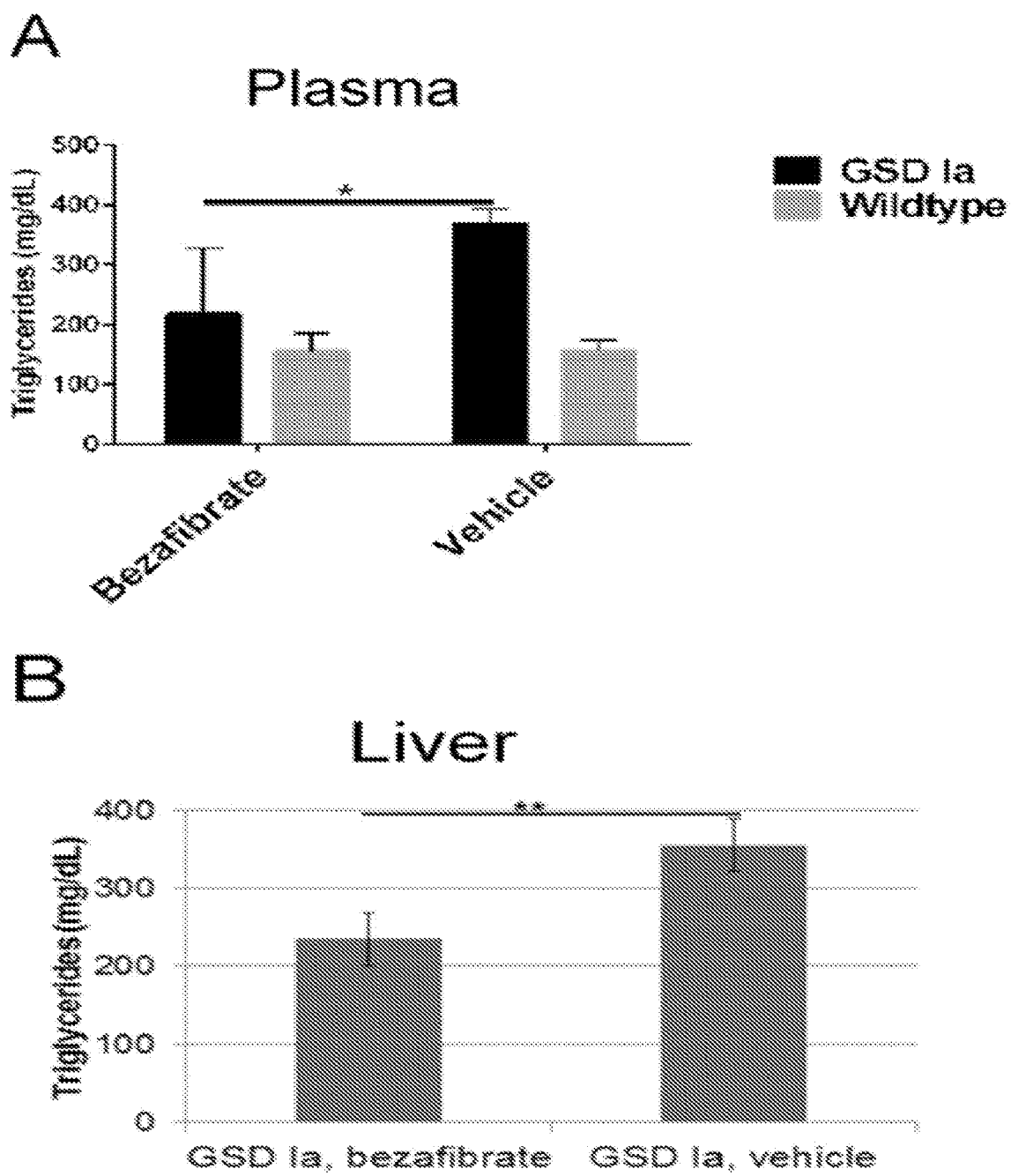
FIG. 30 illustrates treatment of G6Pc−/− mice with bezafibrate reduces plasma triglycerides. Bezafibrate was administered by intraperitoneal injection to groups of 5 day old mice, and triglycerides were quantified 3 days later. (A) plasma, and (B) liver. Groups: bezafibrate, n=5; vehicle, n=3. Mean+/−SD shown. * indicates p<0.05.

The effects of bezafibrate upon autophagy were further demonstrated by decreased plasma triglycerides (FIG. 30A). Similarly, liver triglycerides were reduced in G6Pc−/− mice following bezafibrate administration (FIG. 30B). However, the effect of a single dose of bezafibrate did not reduce liver glycogen content (not shown). These data suggest that the induction of autophagy with bezafibrate was sufficient to decrease the lipid accumulation associated with GSD Ia, which underlies the reduction of autophagy and increase in apoptosis associated with the liver involvement of GSD Ia, features shared with NAFLD. These data promise that drugs such as bezafibrate will reverse the liver effects of GSD Ia at least in part.

The current approach to GSD Ia therapy focuses on preventing lethal hypoglycemia by providing constant calories throughout the day. This fails to prevent many of the chronic symptoms, including hepatomegaly, hyperlipidemia, and glycogen accumulation. While gene therapy approaches appear very promising for long-term treatments and are likely to be extremely beneficial down the line, gene therapy as a treatment field overall is still immature. It takes many years to develop gene therapeutics, and the manufacturing process is still slow and difficult to scale efficiently. As such, stopgap and combinatorial treatments for GSD Ia will be extremely valuable, in that they can provide benefit to patients living with the disease in a much shorter timeframe than can gene therapies.

Autophagy manipulation has only recently been explored as a therapeutic approach to many diseases in which toxic accumulation of endogenous products causes health problems, including prion diseases, Alzheimer's disease, and NAFLD. The theory behind these treatments is that enhanced autophagy may be able to break down the excess products trapped in cells that causes clinical defects. Since much of GSD Ia's symptom set derives from excess lipids, glycogen, and even amino acids, it stands to reason that autophagy could be useful for treating aspects of GSD Ia to reduce the symptoms and improve the quality of life for patients living with it long term.

Figure 2:
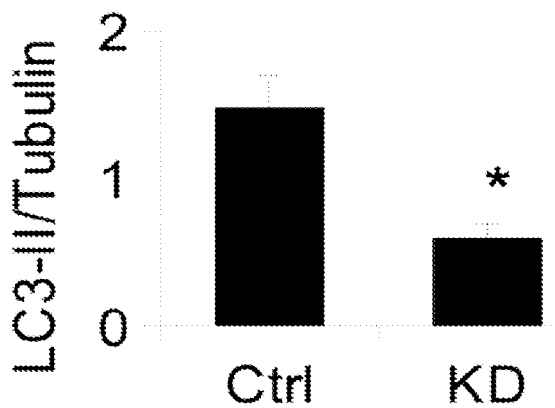
FIG. 2 illustrates that knockdown of G6Pase in AML12 recapitulates GSDIa.
Figure 2:
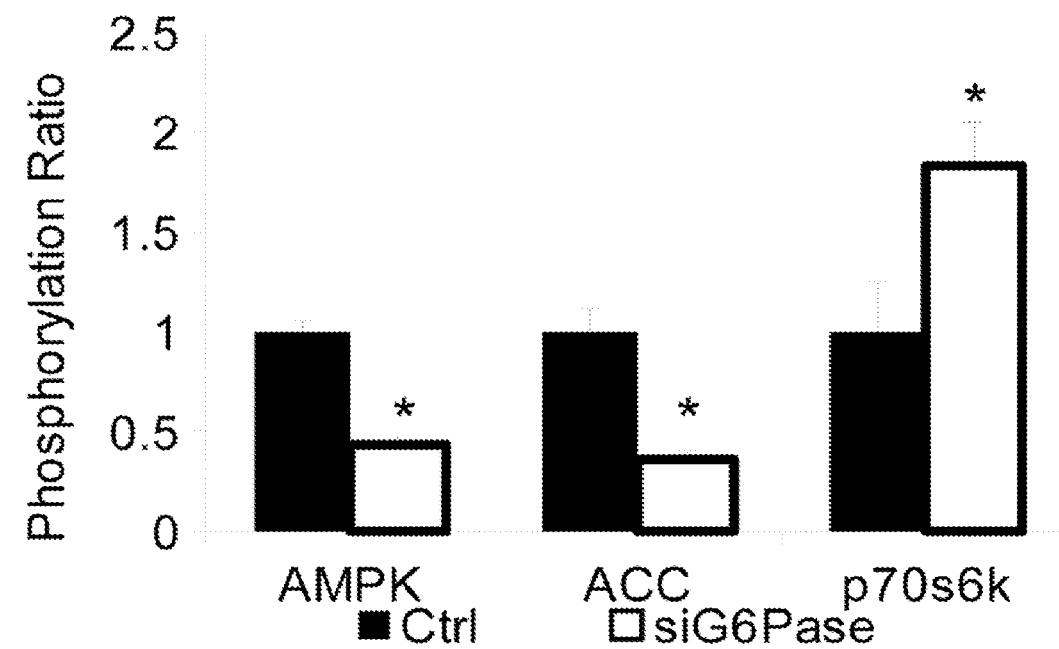
Figure 3:
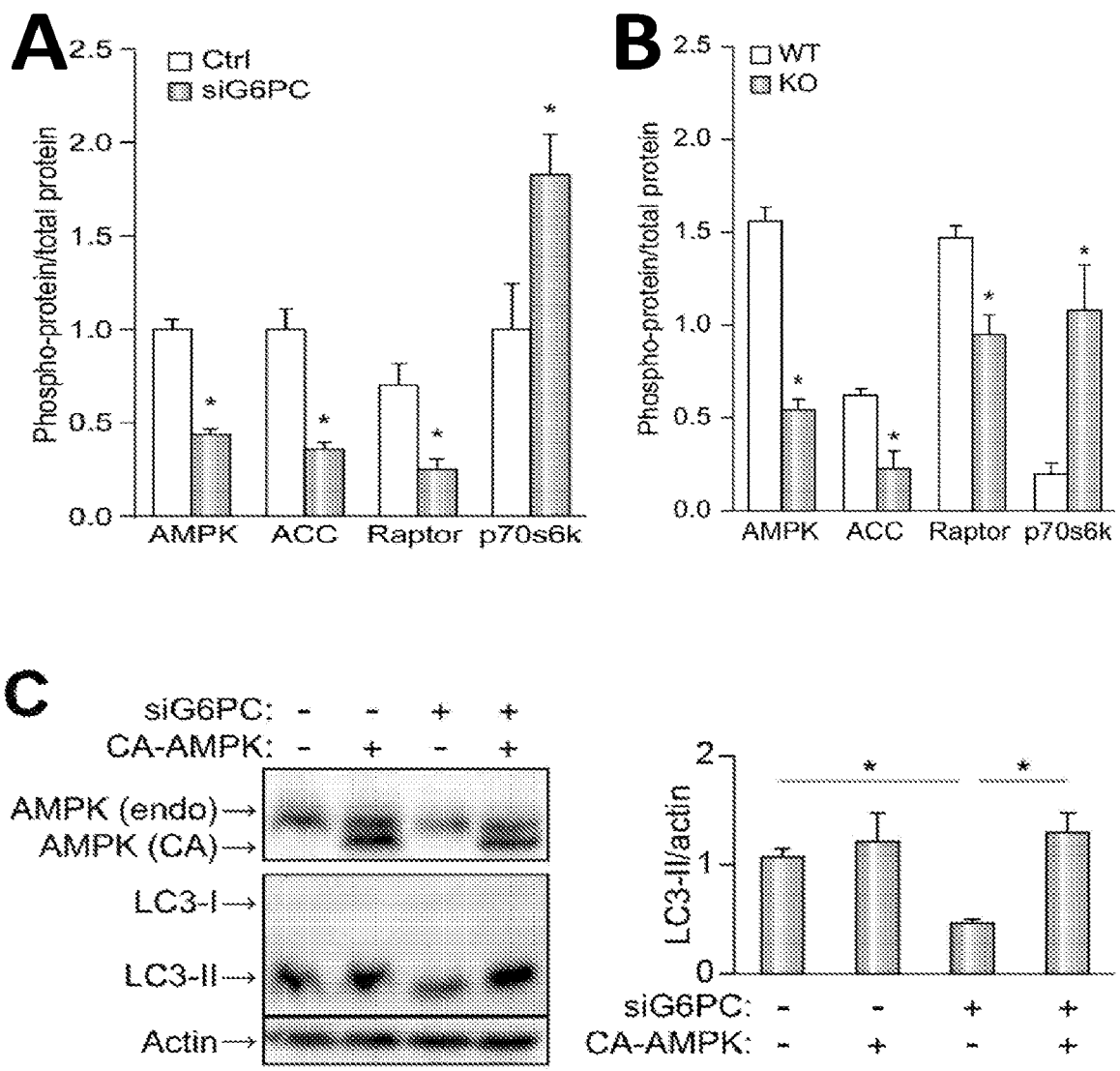
FIG. 3 illustrates that the loss of G6PC inhibits AMPK and activates mTOR signaling, and restoration of AMPK signaling restores autophagy.
Figure 4:
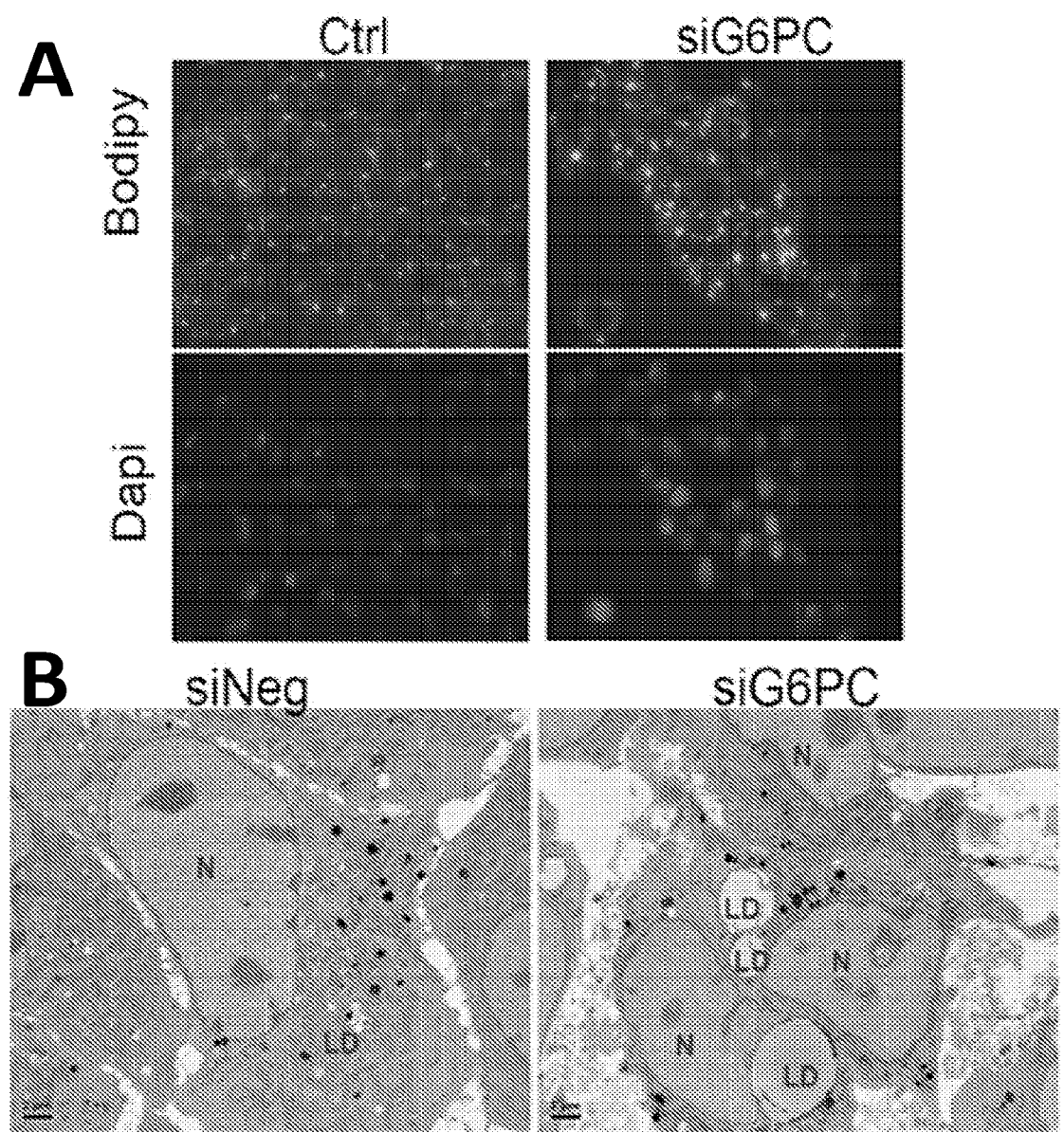
FIG. 4 illustrates lipid accumulation in cells.

In exploring this route, we first found that autophagy is reduced in GSD Ia mice livers and kidneys as well as in the G6pc knockdown AML-12 mouse hepatocyte cell line model (FIGS. 1, 2, and 4). What this meant to us was that increasing autophagy in GSD Ia would not actually mean raising its levels above normal, but rather restoring its levels closer to normal. The distinction means that pro-autophagic treatments are likely to have fewer and less intense side effects in patients, further indicating that this course of treatment investigation is a strong contender for future GSD Ia therapeutics. We believe the autophagic reduction occurs because excess G6P that accumulates as a result of insufficient G6Pase to hydrolyze it signals the cell that the cell is under fed conditions—conditions under which cells try to store excess energy by activating lipogenesis and inhibiting autophagy and fatty acid oxidation. Reversing this state could potentially be done by inhibiting mTORC1 or through other pathways that could out-compete the mTORC1 inhibitory effect.

Using rapamycin, the prototypical mTOR inhibitor to induce autophagy, we confirmed that inhibiting mTORC1 can enhance autophagy in GSD Ia model cells and mice, and that doing so reduces lipid and glycogen accumulation characteristic of GSD Ia (FIGS. 7-14). The effects were further examined in GSD Ia canines by analyzing the reduction in hepatomegaly and liver damage (as indicated by circulating GGT and ALT levels) induced by rapamycin treatment (FIGS. 24-26).

While rapamycin administration showed great effects, its known toxicity, off-target effects, and side effects in humans due to its general inhibition of mTORC1, which controls a wide variety of cellular pathways, makes it a relatively poor option for long-term human treatment. Therefore, we decided the next step was to look for alternative drugs with similar pro-autophagic effects to rapamycin that may produce fewer side effects through long-term administration. We began by using our newly-developed G6pc knockdown AML-12 cell model as a screening system for several drugs with known autophagy-enhancing effects, and analyzed these drugs using Oil Red O staining and LC3 western blots to determine their ability to reduce lipid accumulation in GSD Ia-like cells and confirm their ability to enhance autophagy in the face of GSD Ia (Table 5 and FIG. 27). We found several drugs with pro-autophagic effects in the face of GSD Ia symptoms, and ultimately chose the one with the least toxicity and potential for deleterious side-effects to proceed with in G6pc−/− mice, bezafibrate. This drug has the added benefit of not yet being FDA approved for any kind of therapy in the U.S., but is a well-documented drug approved for use in Europe. This makes it enticing for future research for commercialization because it could be picked up and its research funded by the pharmaceutical industry while already having many toxicity studies completed.

We found that bezafibrate shows trends in enhancing autophagy in GSD 1a mice, but the effect is not significant. However, the study is ongoing and as additional mice are added to treatment groups to increase statistical power, we anticipate the improvements becoming significant. Furthermore, hepatic lipid and glycogen accumulation assays have yet to be performed, and they are planned for the future.

Overall this study has shown that autophagy manipulation has great potential to provide therapeutic benefits for GSD Ia. Rapamycin may not be the best drug for these purposes, but it has opened the door on this new approach. Our small screen has turned up several drugs, and additional screens may reveal yet more as the field of autophagy enhancement grows and more pro-autophagic drugs become known. Ongoing work with bezafibrate is so far promising, and our other top drug candidates, carbamazepine, lithium chloride, and mifepristone, are excellent options to further pursue this course in mouse treatments. We expect that autophagy induction will prove to be an approach rich with new GSD Ia therapies that will be brought to bear in the years to come, dramatically improving the quality of life and clinical outcomes for GSD Ia patients in the near future.

Although the present invention has been described in considerable detail with reference to certain preferred embodiments thereof, other versions are possible. Therefore the spirit and scope of the appended claims should not be limited to the description and the preferred versions contained within this specification.

The invention claimed is:

1. A method of treating a steatosis-associated disorder in a subject, the method comprising: administering to the subject in need thereof an autophagy-inducing agent, wherein the autophagy-inducing agent is a PPAR-α agonist, and wherein the steatosis-associated disorder is Glycogen Storage Disease Type I (GSD I).

2. The method of claim 1, wherein the GSD I is selected from GSD Ia, GSD Ib, or GSD Ic.

3. The method of claim 1, wherein the PPAR-α agonist is selected from a group consisting of bezafibrate, ciprofibrate, gemfibrozil, clofibrate, or a combination thereof.

4. The method of claim 1, wherein the PPAR-α agonist is bezafibrate.

5. The method of claim 1, further comprising administering to the subject a lysosomal enzyme.

6. The method of claim 5, wherein the lysosomal enzyme is acid alpha-glucosidase.

7. A method of reversing steatosis in a subject in need thereof, the method comprising administering to the subject an autophagy-inducing agent, wherein the autophagy-inducing agent is a PPAR-α agonist, wherein the subject has a steatosis-associated disorder, and wherein the steatosis-associated disorder is GSD I.

8. The method of claim 7, wherein the GSD I is selected from GSD Ia, GSD Ib, or GSD Ic.

9. The method of claim 7, wherein the PPAR-α agonist is selected from a group consisting of bezafibrate, ciprofibrate, gemfibrozil, clofibrate, or a combination thereof.

10. The method of claim 7, wherein the PPAR-α agonist is bezafibrate.

11. The method of claim 7, further comprising administering to the subject a lysosomal enzyme.

12. The method of claim 11, wherein the lysosomal enzyme is acid alpha-glucosidase.

13. A method of modulating autophagy in a subject with a steatosis-associated disorder, the method comprising administering to the subject an autophagy-inducing agent, wherein the autophagy-inducing agent is a PPAR-α agonist, and wherein the steatosis-associated disorder is GSD I.

14. The method of claim 13, wherein modulating autophagy is inducing autophagy or promoting autophagy.

15. The method of claim 13, wherein the GSD I is selected from GSD Ia, GSD Ib, or GSD Ic.

16. The method of claim 13, wherein the PPAR-α agonist is selected from a group consisting of bezafibrate, ciprofibrate, gemfibrozil, clofibrate, or a combination thereof.

17. The method of claim 13, wherein the PPAR-α agonist is bezafibrate.

18. The method of claim 13, further comprising administering to the subject a lysosomal enzyme.

19. The method of claim 18, wherein the lysosomal enzyme is acid alpha-glucosidase.

* * * * *